(12) United States Patent
Mátyus et al.

(10) Patent No.: US 8,536,210 B2
(45) Date of Patent: Sep. 17, 2013

(54) COMPOUNDS FOR INHIBITING SEMICARBAZIDE-SENSITIVE AMINE OXIDASE (SSAO)/VASCULAR ADHESION PROTEIN-1 (VAP-1) AND USES THEREOF FOR TREATMENT AND PREVENTION OF DISEASES

(75) Inventors: Péter Mátyus, Budapest (HU); Kálmán Magyar, Budapest (HU); Marjo Pihlavisto, Kaarina (FI); Klára Gyires, Budapest (HU); Norbert Haider, Vienna (AT); Yinghua Wang, Shanghai (CN); Patrick Woda, Vienna (AT); Petra Dunkel, Budapest (HU); Éva Tóth-Sarudy, Budapest (HU); György Túrós, Budapest (HU)

(73) Assignee: Semmelweis Egyetem, Budapest (HU)

( * ) Notice: Subject to any disclaimer, the term of this patent is extended or adjusted under 35 U.S.C. 154(b) by 0 days.

(21) Appl. No.: 13/063,224

(22) PCT Filed: Sep. 11, 2009

(86) PCT No.: PCT/HU2009/000082
§ 371 (c)(1),
(2), (4) Date: May 25, 2011

(87) PCT Pub. No.: WO2010/029379
PCT Pub. Date: Mar. 18, 2010

(65) Prior Publication Data
US 2011/0263567 A1 Oct. 27, 2011

(30) Foreign Application Priority Data
Sep. 11, 2008 (HU) .................................. 0800563

(51) Int. Cl.
*A01N 43/76* (2006.01)
*A61K 31/42* (2006.01)
*C07D 263/02* (2006.01)

(52) U.S. Cl.
USPC .......................................... 514/374; 548/215

(58) Field of Classification Search
USPC .......................................... 548/215; 514/374
See application file for complete search history.

(56) References Cited

U.S. PATENT DOCUMENTS
2003/0163001 A1 8/2003 Wurziger et al.

FOREIGN PATENT DOCUMENTS
EP 0 038 061 A1 10/1981
JP 2009-132675 A 6/2009
WO 01/74760 A1 10/2001

OTHER PUBLICATIONS

Vippagunta et al (2001).*
Baker et al.: "Derivatives of 1:2:3:4-Tetrahydroxybenzene. Part IV. Attempted Syntheses.", J Chem Soc, 1938, pp. 372-375.
Desai et al.: "Oxone as an Inexpensive, Safe, and Environmentally Benign Oxidant for C—H Bond Oxygenation", Organic Letters, 2006, vol. 8, No. 6, pp. 1141-1144.
Lee et al.: "An Efficient Synthesis of Bensopyrano-2-Isoxazolines", Synthetic Communications, 1996, vol. 26, No. 17, pp. 3201-3215.
Matyus et al.: "Semicarbazide-Sensitive Amine Oxidase: Current Status and Perspectives", Current Medicinal Chemistry, 2004, vol. 11, pp. 1285-1298.
Dunkel et al.: "Semicarbazide-Sensitive Amine Oxidase/Vascular Adhesion Protein 1: Recent Developments Concerning Substrates and Inhibitors of a Promising Therapeutic Target", Current Medicinal Chemistry, 2008, vol. 15, pp. 1827-1839.
Surya et al.: "An Easy Construction of 8,12-Dioxa-13-azatricyclo[8,3,1,02,7]tetradeca-2(7),3,5,13-tetraen-14-ones", Tetrahedron Letters, 1998, vol. 39, pp. 2389-2390.
Ishihara et al.: "Rhenium(VII) Oxo Complexes as Extremely Active Catalysts in the Dehydration of Primary Amides and Aldoximes to Nitriles", Agnew. Chem. Int. Ed., 2002, vol. 41, No. 16, pp. 2983-2986.

* cited by examiner

*Primary Examiner* — Paul V. Ward
(74) *Attorney, Agent, or Firm* — Jason D. Voight

(57) ABSTRACT

The present invention relates to compounds of general formula (i) having an oxime moiety or a pharmaceutically acceptable salt, hydrate or solvate thereof and its use for inhibiting semicarbazide-sensitive amine oxidase (SSAO), also known as vascular adhesion protein-1 (VAP-1), a pharmaceutical composition comprising the compound or a salt, hydrate or solvate thereof as an active ingredient, a method for the prevention or the treatment of a SSAO/VAP-1 related disease, said diseases including acute or chronic inflammatory diseases, diseases related to carbohydrate metabolism, diabetes-associated complications, diabetic retinopathy and macular oedema, diseases related to adipocyte or smooth muscle dysfunctions, neurodegenerative diseases and vascular diseases.

12 Claims, No Drawings

COMPOUNDS FOR INHIBITING SEMICARBAZIDE-SENSITIVE AMINE OXIDASE (SSAO)/VASCULAR ADHESION PROTEIN-1 (VAP-1) AND USES THEREOF FOR TREATMENT AND PREVENTION OF DISEASES

This is the National Stage of International Application PCT/HU2009/000082, filed Sep. 11, 2009.

FIELD OF THE INVENTION

The present invention relates to a compound having an oxime moiety or a pharmaceutically acceptable salt, hydrate or solvate thereof and its use for inhibiting semicarbazide-sensitive amine oxidase (SSAO), also known as vascular adhesion protein-1 (VAP-1), a pharmaceutical composition comprising the compound or a salt, hydrate or solvate thereof as an active ingredient, a method for the prevention or the treatment of a SSAO/VAP-1 related disease, said diseases including acute or chronic inflammatory diseases, diseases related to carbohydrate metabolism, diabetes-associated complications, diabetic retinopathy and macular oedema, diseases related to adipocyte or smooth muscle dysfunctions, neurodegenerative diseases and vascular diseases.

BACKGROUND OF THE RELATED ART

Semicarbazide sensitive amine oxidase (SSAO)/vascular adhesion protein-1 (VAP-1) is a membrane protein with a dual function. On the one hand, SSAO [EC 1.4.3.6.] belongs to the family of copper-containing amine oxidases, its name deriving from its sensitivity to inhibition by the carbonyl reagent, semicarbazide (Lyles G A, Int. J. Biochem. Cell. Biol., 1996, 28, 259-274). SSAO catalyzes the oxidative deamination of primary aliphatic and aromatic amines with the following reaction pathway.

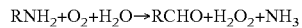

The enzymatic reaction of the amine results in the formation of the corresponding aldehyde, $H_2O_2$ and ammonia; the products formed in the reaction being generally more cytotoxic than the substrates themselves. For the human enzyme, aminoacetone and methylamine have been identified as endogenous physiological substrates.

On the other hand, analysis of the genetic encoding of an adhesion protein revealed the identity of SSAO and human vascular adhesion protein-1 (VAP-1) (Smith D J et al, J. Exp. Med., 1998, 188, 17-27). VAP-1 is a cell adhesion molecule with some special features distinguishing it from other adhesion molecules related to inflammation, such as the monoamine oxidase activity and a restricted expression pattern (Salmi M et al, Science, 1992, 257, 1407-1409; Smith D J et al, J. Exp. Med., 1998, 188, 17-27). The level of VAP-1 is upregulated in the vasculature at sites of inflammation.

Although the substrate specificity of SSAO/VAP-1 partly overlaps with that of monoamine oxidases (MAOs), SSAO/VAP-1 differs from MAO A and MAO B with respect to cofactor (2,4,5-trihydroxy-phenylalanyl quinone (TPQ) for SSAO/VAP-1), biological function, substrates, inhibitors and subcellular distribution. Products of SSAO/VAP-1, such as formaldehyde are mainly extracellular. The absence of formaldehyde dehydrogenase from the blood plasma, where SSAO/VAP-1 products are formed, may amplify the potential toxic effects of formaldehyde towards blood vessels.

SSAO/VAP-1 exists as a membrane-bound and as a soluble form in the plasma, its activity displaying a wide tissue distribution. It has been hypothesized that the soluble form is generated via proteolytic cleavage from the membrane-bound form. The major sources of the enzyme are the endothelial cells, smooth muscle cells and adipocytes. Because expression of SSAO is particularly remarkable in the endothelium and the plasma, cytotoxic effects associated with the enzyme may be increased in the highly vascularised tissues, such as the eyes and kidneys, partially explaining late-diabetic complications (Ekblom J. et al, Pharmacol. Res., 1998, 37, 87-92).

SSAO/VAP-1 has a role in the metabolism of biogenic and xenobiotic amines. Products formed in the enzyme reaction (formaldehyde, methylglyoxal and $H_2O_2$ for the endogenous substrates) may be involved in processes such as protein cross-linking, formation of advanced-glycation end products or increase of oxidative stress. Higher concentrations of the physiological substrates in diabetes together with the higher enzyme activity observed may lead to a higher production of the cytotoxic agents, therefore may lead to diabetes-associated complications. Treatment of diabetes-associated vasculopathies such as retinopathy, neuropathy and nephropathy with enzyme inhibitors has been proposed.

SSAO/VAP-1 expression is induced during adipogenesis (Fontana E et al, Biochem. J., 2001, 356, 769-777; Moldes M et al, J. Biol. Chem., 1999, 274, 9515-9523), therefore a role for SSAO/VAP-1 in the adipogenic gene program has been suggested. Due to its special features in adipose tissue, SSAO/VAP-1 has been proposed as potential target for the treatment of obesity (Bour S et al, Biochimie, 2007, 89, 916-925).

SSAO/VAP-1 as an adhesion molecule plays a role in leukocyte trafficking and is involved in an adhesive cascade leading to the transmigration of leukocytes into inflamed tissues from the circulation. In the adhesion cascade both the amine oxidase and the adhesive function of SSAO/VAP-1 take part (Salmi M et al, Immunity, 2001, 14, 265-276), a direct interaction with a leukocyte surface substrate mediating the leukocyte-SSAO/VAP-1 interaction has been proposed. Products of the enzyme reaction of SSAO/VAP-1, such as $H_2O_2$, a signalling molecule itself, via the upregulation of other adhesion molecules leading to enhanced leukocyte trafficking may contribute to the escalation of the inflammatory process. Therefore, inhibitors of the enzymatic activity may serve as useful antiinflammatory agents.

SSAO/VAP-1 inhibitors could reduce leukocyte trafficking at sites of inflammation and therefore reduce the inflammatory process as proved by several animal studies (for example: ulcerative colitis—Salter-Cid L M et al, J. Pharm. Exp. Ther., 2005, 315, 553-562; arthritis—Marttila-Ichihara F et al, Arthritis Rheum., 2006, 54, 2852-282862; multiple sclerosis—Wang E Y et al, J. Med. Chem., 2006, 49, 2166-2173; uveitis—Noda K et al, FASEB J., 2008, 22, 1094-1103). As translocation of VAP-1 to the endothelial cell surface occurs at sites of inflammation, modulation of the normal immune system could be avoided by the use of SSAO/VAP-1 as a novel anti-inflammatory target.

In healthy humans, the plasma SSAO/VAP-1 activity is rather constant. Elevated SSAO/VAP-1 levels or overexpression of the enzyme have been observed in various pathological conditions or diseases, such as diabetes (both type I and type II), particularly in the presence of diabetic complications (Boomsma F et al, Biochim Biophys. Acta, 2003, 1647, 48-54; Boomsma F, Clin. Sci., 1995, 88, 675-679; Garpenstrand H et al, Diabetic. Med., 1999, 16, 514-521; Meszaros Z et al, Metab. Clin. Exp., 1999, 48, 113-117; Boomsma F et al, Diabetologia, 1999, 42, 233-237; Salmi M et al, Am. J. Pathol., 2002, 161, 2255-2262), congestive heart failure (Boomsma F et al, Cardiovasc. Res., 1997, 33, 387-391), obesity (Meszaros Z et al, Metab. Clin. Exp., 1999, 48, 113-117; Weiss H G et al, Metab. Clin. Exp., 2003, 52, 688-692), end-stage renal disease (Kurkijarvi R et al, Eur. J. Immunol., 2001, 31, 2876-2884), multiple sclerosis (Airas L et al, J. Neuroimmunol., 2006, 177, 132-135), inflammatory liver diseases (Kurkijarvi R et al, J. Immunol., 1998, 161, 1549-1557), psoriasis (Madej A et al, J. Eur. Acad. Dermatol. Venereol., 2007, 21, 72-78), Alzheimer's disease (del Mar Hernandez M et al, Neurosci. Lett., 2005, 384, 183-187; Ferrer I et al, Neurosci. Lett., 2002, 321, 21-24) and myopathies (Olive M et al, Muscle Nerve, 2004, 29, 261-266). A role for SSAO/VAP-1 in apoptosis, possibly leading to vascular tissue damage and atherogenesis has been implicated.

An oxime prodrug approach for ketone drugs, the nonsteroidal antiinflammatory drugs ketoprofen and nabumetone has been reported recently (Kumpulainen H, J. Med. Chem., 2006, 49, 1207-1211). The oxime structure was activated to the ketone with simultaneous release of nitric oxide (NO).

Because of its proposed involvement in a number of inflammatory processes and various pathologies, there is a great demand for inhibitors of SSAO/VAP-1 that can have therapeutic value in the prevention or the treatment of disorders or diseases associated with an elevated level or overexpression of SSAO/VAP-1, said diseases involving acute and chronic inflammations, diseases related to carbohydrate metabolism, diabetes-associated complications, diabetic retinopathy and macular oedema, diseases related to adipocyte or smooth muscle dysfunctions, neurodegenerative diseases and vascular diseases.

Several small-molecule inhibitors of SSAO/VAP-1 have been identified: hydrazine derivatives, phenylallylhydrazines (WO2006/094201, WO2005/014530), hydrazino alcohols and hydrazino indanes (WO2002/0202090, WO2003/006003, WO2005/080319), arylalkylamines, propenyl- and propargylamines, oxazolidinones, haloalkylamines, 1,3,4-oxadiazines (WO2002/0202541), 4,5,6,7-tetrahydroimidazo[4,5-c]pyridines (WO2002/0238153), thiocarbamoyl derivatives, carboxamides and sulfonamides (WO2006/013209, US2007/066646), thiazole derivatives (WO2004/087138, WO2004/067521, WO2006/028269, WO2006/011631), compounds disclosed in WO2005/082343; (compounds reviewed in: Matyus P et al, Curr. Med. Chem., 2004, 11, 1285-1298; Dunkel P et al, Curr. Med. Chem., 2008, 15, 1827-1839). Further relevant documents are mentioned in "Disclosure of the Invention" part hereinbelow.

We now found that a special class of compounds, containing an oxime group and an unsaturated ring system joining to the carbon atom of the oxime group, optionally through an alkylene moiety, exhibit SSAO/VAP-1 inhibitory and antiinflammatory effects. Some of the compounds are novel.

DISCLOSURE OF THE INVENTION

The present invention relates to a compound of general formula of Ar—$(CH_2)_n$—$CR^1$=N—$OR^2$ (I) or salt, hydrate or solvate thereof, wherein
Ar is a group of the formula:

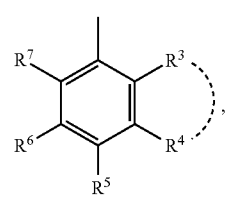
(a)

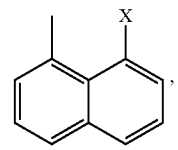
(b)

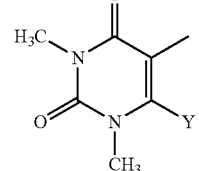
(c)

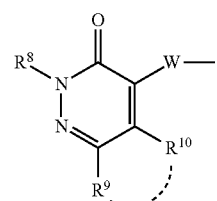
(d)

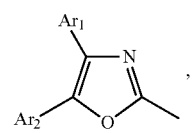
(e)

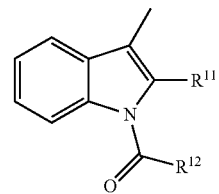
(f)

$R^1$ is H or lower alkyl;
$R^2$ is H, lower alkyl, benzyl, —$(CH_2)_k$—$COOR^{13}$, —$(CH_2)_m$—$N(R^{14}R^{15})$ or —CO—NH—$R^{16}$,
wherein $R^{13}$ is lower alkyl,
k is 1, 2 or 3, preferably 1;
m is 1, 2 or 3; preferably 2;
$R^{14}$ and $R^{15}$ are independently from each other lower alkyl, or $R^{14}$ and $R^{15}$ together with the nitrogen they are attached form a 5 to 7 membered heteroring, optionally containing 1 to 3 further heteroatom(s) selected from nitrogen, oxygen and sulfur atoms,
$R^{16}$ is phenyl, optionally substituted with one or more group selected from halogen, lower alkyl and lower alkoxy;

$R^3$ and $R^4$ together with the carbons they are attached to form a 5 to 7 membered heterering containing one or two oxygen(s), preferably 1,3-dioxolane, optionally substituted with lower alkyl, preferably with methyl; or $R^3$ is H, halogen, lower alkyl or $OR^{17}$, wherein $R^{17}$ is H, lower alkyl, lower alkenyl, optionally substituted with phenyl;

$R^4$ is H or $OR^{19}$, wherein $R^{19}$ is lower alkyl;

$R^5$ is H or halogen;

$R^6$ is H or halogen;

$R^7$ is H, halogen, OH, $OR^{20}$ or a phenyl substituted with Z, wherein $R^{20}$ is lower alkyl or lower alkenyl, and Z is —CH=N—OH or halogen;

provided that if Ar is substituted phenyl of group (a), then
the phenyl ring has at least one halogen and one allyloxy substituent, excluding the following substitution patterns of the phenyl ring: if n=0, $R^2$=H and $R^1$=H: 2-allyloxy-4-bromo (see in WO2001074760), 2-allyloxy-5-bromo (see in JP2009132675), 2-allyloxy-5-chloro (see in Synth. Comm., 1996, 26(17), 3201-3215), 4-allyloxy-3-chloro, commercially available; or if n=0, $R^2$=H and $R^1$=CH$_3$: 2-allyloxy-5-chloro (see in Tetrahedron Lett., 1998, 39(16), 2389-2390); or the phenyl ring has at least one methyl and one alkoxy substituent, excluding the following substitution patterns of the phenyl ring: if n=0, $R^2$=H and $R^1$=H: 2-methoxy-6-methyl, commercially available; or if n=0, $R^2$=CH$_3$ and $R^1$=H: 2-methoxy-6-methyl (see in Org. Lett., 2006, 8(6), 1141-1144); or the phenyl ring has one (2-phenylprop-2-ene-1-yl)oxy substituent;

X is a 5 to 7 membered heterering containing 1 or 3 heteroatom(s) selected from nitrogen, oxygen and sulfur atoms;

Y is $SR^{21}$, $OR^{22}$, 5 to 7 membered heterering containing 1 to 3 heteroatom(s) selected from nitrogen, oxygen and sulfur atoms, optionally substituted with phenyl or a (lower alkenyl) amino, optionally N-substituted with lower alkyl; wherein $R^{21}$ is lower alkyl or phenyl and $R^{22}$ is lower alkyl;

$R^8$ is lower alkyl or optionally substituted benzyl, wherein the substituent is 1 or 2 lower alkoxy, preferably methoxy;

$R^9$ is H or phenyl;

$R^{10}$ is di(lower alkyl)amino, preferably dimethylamino, 5 to 7 membered heterering containing 1 or 3 heteroatom(s) selected from nitrogen, oxygen and sulfur atoms, optionally substituted with one or more group selected from lower alkyl, lower alkenyl and phenyl;

or $R^9$ and $R^{10}$ together with the attached carbon atoms form an optionally substituted 5 to 8 membered heterering containing 1 or 3 heteroatom(s) selected from nitrogen, oxygen and sulfur atoms, optionally substituted with one or more group selected from lower alkyl and benzyl, and optionally together with lower alkylene form a fused bicyclic group;

W is a bond or a phenylene group, preferably 1,2-phenylene group;

$R^{11}$ is lower alkyl;

$R^{12}$ is phenyl, optionally substituted with halogen; preferably with chloro;

n is integer of 0 to 4, preferably 0, 1 or 2;

$Ar^2$ and $Ar^2$ are the same or different and stand for phenyl, optionally substituted with one or more group selected from halogen, lower alkyl and lower alkoxy, preferably both are phenyl;

with the proviso that:
when n=0, $R^1$=H, $R^2$=H and Ar=2,4-dichlorophenyl, then Z is not 4-fluoro (see in EP0038061); and when n=0, $R^1$=H, $R^2$=H, $R^3$+$R^4$=—O—CH$_2$—O—, then one of $R^5$, $R^6$ and $R^7$ is not H (see in Angew. Chem., 2002, 41(16), 2983-2986); and when $R^1$=CH$_3$, $R^2$=H, $R^4$+$R^3$=—O—CH$_2$—O— and $R^6$=$R^7$=H, then $R^5$ is not methoxy (see in J. Chem. Soc., 1938, 372-5);

and any stereoisomer, mixture of stereoisomers, E or Z forms, mixture of E and Z forms, prodrug, metabolite, crystalline form, non-crystalline form thereof.

The above compounds are useful for inhibiting SSAO enzyme activity and/or for inhibiting binding to VAP-1.

Preferred compounds are the following ones:

Those compounds of general formula (I), wherein $R^{14}$ and $R^{15}$ are methyl, or $R^{14}$ and $R^{15}$ together with the nitrogen they are attached to form a pyrrolidine ring.

Those compounds of general formula (I), wherein $R^3$ is methyl, allyloxy or (2-phenylprop-2-ene-1-yl)oxy.

Those compounds of general formula (I), wherein Y is phenylpiperazino or a (lower alkenyl)-amino N-substituted with lower alkyl, preferably allyl(methyl)amino.

Those compounds of general formula (I), wherein $R^{16}$ is pyrrolidino, piperidino, morpholino or piperazino substituted with methyl or phenyl.

Those compounds of general formula (I), wherein $R^9$ and $R^{10}$ together with the attached carbon atoms form an 6-7 membered heterering, preferably a 1,4-oxazine or 1,4-oxazepine, or optionally substituted with one or more group selected from methyl and benzyl, optionally fused with $C_3$ alkylene to form a bicyclic group.

Preferred compounds are the following ones:

3-methoxy-2-methylbenzaldehyde oxime;
8-Pyrrolidino-1-naphthaldehyde oxime;
5-Hydroxy-1,3-benzodioxole-4-carbaldehyde oxime;
5-Ethoxy-1,3-benzodioxole-4-carbaldehyde oxime;
5-(Allyloxy)-1,3-benzodioxole-4-carbaldehyde oxime;
5-Bromo-1,3-benzodioxole-4-carbaldehyde oxime;
5-{2-[(Hydroxyimino)methyl]phenyl}-1,3-benzodioxole-4-carbaldehyde oxime;
6-Ethoxy-1,3-dimethyl-2,4-dioxo-1,2,3,4-tetrahydropyrimidine-5-carbaldehyde oxime;
6-Methoxy-1,3-dimethyl-2,4-dioxo-1,2,3,4-tetrahydropyrimidine-5-carbaldehyde oxime;
1,3-Dimethyl-2,4-dioxo-6-propoxy-1,2,3,4-tetrahydropyrimidine-5-carbaldehyde oxime;
6-Ethoxy-1,3-dimethyl-2,4-dioxo-1,2,3,4-tetrahydropyrimidine-5-carbaldehyde-O-methyloxime;
1,3-Dimethyl-2,4-dioxo-6-(propylthio)-1,2,3,4-tetrahydropyrimidine-5-carbaldehyde oxime;
1,3-Dimethyl-6-(methylthio)-2,4-dioxo-1,2,3,4-tetrahydropyrimidine-5-carbaldehyde oxime;
6-(Ethylthio)-1,3-dimethyl-2,4-dioxo-1,2,3,4-tetrahydropyrimidine-5-carbaldehyde oxime;
1,3-Dimethyl-2,4-dioxo-6-(phenylthio)-1,2,3,4-tetrahydropyrimidine-5-carbaldehyde oxime;
6-(Ethylthio)-1,3-dimethyl-2,4-dioxo-1,2,3,4-tetrahydropyrimidine-5-carbaldehyde-O-methyloxime;
6-[Allyl(methyl)amino]-1,3-dimethyl-2,4-dioxo-1,2,3,4-tetrahydropyrimidine-5-carbaldehyde oxime;
3-(4,5-Diphenyl-1,3-oxazol-2-yl)propanal oxime (more preferred compound) and
1-(4-Chlorobenzoyl)-2-methyl-1H-indole-3-carbaldehyde oxime (more preferred compound),
or any stereoisomer, mixture of stereoisomers, E or Z forms, mixture of E and Z forms, prodrug, metabolite, crystalline form, non-crystalline form, hydrate, solvate or salt thereof.

The present invention also relates to compounds of general formula (I) or a pharmaceutically acceptable salt thereof for use as medicament.

In a specially advantageous embodiment of the invention the compound of general formula (I) possessing SSAO/VAP-1 inhibitory activity is a prodrug of another active ingredient, i.e. the compounds of general (I) can be converted through metabolism into molecules having another type therapeutical activity under in vivo conditions. Preferred embodiment of this SSAO/VAP-1 inhibitor oxime prodrug approach is the use of oxime derivatives that can be metabolized in vivo to molecules exhibiting antiinflammatory effects. Moreover, SSAO/VAP-1-inhibiting oxime compounds can display other valuable biological activities, such as NO donor properties. In this preferred embodiment both the compound of general formula (I) and metabolite of it have valuable therapeutical activity which activities are advantageous in case of the disease to be treated.

For example 3-(4,5-diphenyl-1,3-oxazol-2-yl)propanal oxime and 1-(4-chlorobenzoyl)-2-methyl-1H-indole-3-carbaldehyde oxime were prepared to utilize, besides their valuable SSAO inhibitory and possible NO donor properties, also the antiinflammatory effects of their carboxylic acid analogs. Namely, 3-(4,5-diphenyl-1,3-oxazol-2-yl)propionic acid and 1-(4-chlorobenzoyl)-2-methyl-1H-indole-3-carboxylic acid, possessing excellent known antiinflammatory activities, can be formed from 3-(4,5-diphenyl-1,3-oxazol-2-yl)propanal oxime and 1-(4-chlorobenzoyl)-2-methyl-1H-indole-3-carbaldehyde oxime, respectively, under in vivo conditions via known metabolic processes including hydrolysis and subsequent oxidation of the carbaldehyde formed to carboxylic acid (accordingly, these compounds are especially preferred compounds).

The present invention also provides pharmaceutical composition, which comprises, as an active ingredient, one or more compound(s) of general formula (I) or a pharmaceutically acceptable salt thereof in admixture with one or more pharmaceutically acceptable auxiliary/auxiliaries.

The pharmaceutical compositions of the invention comprise a therapeutically effective amount of one or more of the compounds of formula (I) and a pharmaceutically acceptable carrier, preferably in human unit dosages.

The present invention also relates to the use of a compound of general formula of Ar—$(CH_2)_n$—$CR^1$=N—$OR^2$ (I') or salt, hydrate or solvate thereof—wherein Ar is a group of the formula:

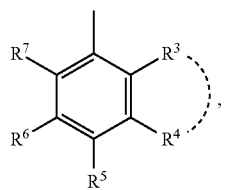

(a)

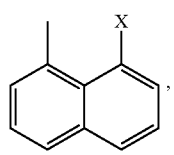

(b)

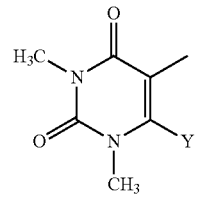

(c)

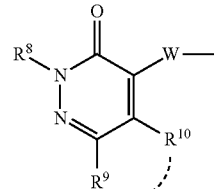

(d)

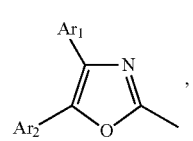

(e)

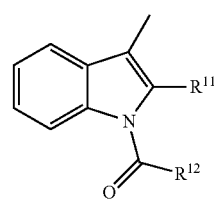

(f)

$R^1$ is H or lower alkyl;
$R^2$ is H, lower alkyl, benzyl, —$(CH_2)_k$—$COOR^{13}$, —$(CH_2)_m$—$N(R^{14}R^{15})$ or —CO—NH—$R^{16}$,
  wherein $R^{13}$ is lower alkyl,
  k is 1, 2 or 3, preferably 1;
  m is 1, 2 or 3; preferably 2;
  $R^{14}$ and $R^{15}$ are independently from each other lower alkyl, or $R^{14}$ and $R^{15}$ together with the nitrogen they are attached form a 5 to 7 membered heteroring, optionally containing 1 to 3 further heteroatom(s) selected from nitrogen, oxygen and sulfur atoms,
  $R^{16}$ is phenyl, optionally substituted with one or more group selected from halogen, lower alkyl and lower alkoxy;
$R^3$ and $R^4$ together with the carbons they are attached to form a 5 to 7 membered heteroring containing one or two oxygen(s), preferably 1,3-dioxolane, optionally substituted with lower alkyl, preferably with methyl; or
$R^3$ is H, halogen, lower alkyl or $OR^{17}$, wherein $R^{17}$ is H, lower alkyl, lower alkenyl, optionally substituted with phenyl;
$R^4$ is H or $OR^{19}$, wherein $R^{19}$ is lower alkyl;
$R^5$ is H or halogen;
$R^6$ is H or halogen;
$R^7$ is H, halogen, OH, $OR^{20}$ or a phenyl substituted with Z wherein $R^{20}$ is lower alkyl or lower alkenyl, and Z is —CH=N—OH or halogen;
X is a 5 to 7 membered heteroring containing 1 or 3 heteroatom(s) selected from nitrogen, oxygen and sulfur atoms;
Y is $SR^{21}$, $OR^{22}$, 5 to 7 membered heteroring containing 1 to 3 heteroatom(s) selected from nitrogen, oxygen and sulfur atoms, optionally substituted with phenyl or a (lower alkenyl) amino, optionally N-substituted with lower alkyl; wherein $R^{21}$ is lower alkyl or phenyl and $R^{22}$ is lower alkyl;

$R^8$ is lower alkyl or optionally substituted benzyl, wherein the substituent is 1 or 2 lower alkoxy, preferably methoxy;

$R^9$ is H or phenyl;

$R^{10}$ is di(lower alkylamino, preferably dimethylamino, 5 to 7 membered heteroring containing 1 or 3 heteroatom(s) selected from nitrogen, oxygen and sulfur atoms, optionally substituted with one or more group selected from lower alkyl, lower alkenyl and phenyl;

or $R^9$ and $R^{19}$ together with the attached carbon atoms form an optionally substituted 5 to 8 membered heteroring containing 1 or 3 heteroatom(s) selected from nitrogen, oxygen and sulfur atoms, optionally substituted with one or more group selected from lower alkyl and benzyl, and optionally together with lower alkylene form a fused bicyclic group;

W is a bond or a phenylene group, preferably 1,2-phenylene group;

$R^{11}$ is lower alkyl;

$R^{12}$ is phenyl, optionally substituted with halogen; preferably with chloro;

n is integer of 0 to 4, preferably 0, 1 or 2;

$Ar^1$ and $Ar^2$ are the same or different and stand for phenyl, optionally substituted with one or more group selected from halogen, lower alkyl and lower alkoxy, preferably both are phenyl;

and any stereoisomer, mixture of stereoisomers, E or Z forms, mixture of E and Z forms, prodrug, metabolite, crystalline form, non-crystalline form thereof—in the preparation of medicament or pharmaceutical composition for the prevention or treatment of a SSAO/VAP-1 related disease.

The reference to all the possible E- and Z-isomers (and the mixtures thereof) and the preferred compounds are the same as defined hereinbefore for compounds of general formula (I).

The present invention also relates to compounds of general formula (I') for use in the treatment or prevention of a SSAO/VAP-1 related disease.

The present invention also relates to method of treatment or prevention of a SSAO/VAP-1 related disease comprising administering a therapeutically effective amount of one or more compound(s) of general formula (I') or a pharmaceutically acceptable salt thereof to a mammal in the need thereof.

The above compounds, use and method of prevention and treatment may be therapeutically beneficial in inflammatory diseases and conditions and in various other pathologies, including diseases related to carbohydrate metabolism, diabetes-associated complications, diabetic retinopathy, macular oedema, diseases related to adipocyte or smooth muscle dysfunctions, neurodegenerative diseases and vascular diseases.

With other words, the present invention relates to a method for the prevention or the treatment of diseases related to elevated levels of SSAO/VAP-1, by administering compounds to inhibit SSAO/VAP-1 enzyme activity and/or to inhibit binding to SSAO/VAP-1 in a therapeutically effective amount or by administering a therapeutically effective combination of SSAO/VAP-1 inhibitors.

In a preferred embodiment, the invention relates to a method of using the compounds provided in the invention for inhibiting SSAO/VAP-1 enzyme activity and/or inhibiting binding to SSAO/VAP-1 in vitro.

In another preferred embodiment, the invention relates to a method of using the compounds provided in the invention for inhibiting SSAO/VAP-1 enzyme activity and/or inhibiting binding to SSAO/VAP-1 in vivo, e.g. in an assay.

DETAILED DESCRIPTION OF THE INVENTION

The term "halogen" as used herein refers to the Group VIIa elements and includes Cl, Br, F and I substituents. Preferred halogen substituents are Cl and F.

The term "lower alkyl" in the meaning of an alkyl group refers to aliphatic and alicyclic groups including straight-chain (linear), branched-chain or cyclic groups having up to 6, preferably 4 carbon atoms; methyl and ethyl are more preferred.

The term "lower alkenyl" refers to unsaturated aliphatic and alicyclic groups including straight-chain (linear), branched-chain, cyclic groups, and combinations thereof, having up to 6, preferably 4 carbon atoms, which contain at least one double bond (—C═C—). Preferred example of alkenyl group is the allyl group (—$CH_2$—CH═$CH_2$).

The term "lower alkoxy" refers to a "(lower alkyl)-O—" group (where the "lower alkyl" has the above-defined meaning). Examples of alkoxy groups include, but are not limited to, groups such as methoxy, ethoxy, propyloxy (either n-propoxy or i-propoxy), and butoxy (either n-butoxy, i-butoxy, sec-butoxy, or tert-butoxy). A particularly preferred alkoxy substituent is methoxy.

The definition of "5 to 7" (or 5 to 8) membered heteroring, optionally containing 1 to 3 further heteroatom(s) selected from nitrogen, oxygen and sulfur atoms" relates to any saturated or unsaturated 5 to 7 (or 5 to 8) membered heteroring, optionally containing 1 to 3 further heteroatom(s) selected from nitrogen, oxygen and sulfur atoms. In a preferred embodiment the heteroring is saturated, and stands for preferably 5 or 6 ring atoms, wherein 1 or 2 ring members are selected from the group consisting of O, S and N and the remaining atoms are carbon. However, when $R^9$ and $R^{10}$ together with the attached carbon atoms form a ring, the 7-membered 1,4-oxazepine is also preferred. Non-limiting examples of the preferred rings are piperidine, pyrrolidine, piperazine, oxazine, preferably 1,4-oxazine (morpholine), oxazepine, preferably 1,4-oxazepine, thiomorpholine, thiazolidine, dioxolane, tetrahydrofurane, tetrahydrothiophene and tetrahydrothiopyrane.

The definition of "5 to 7" membered heteroring containing one or two oxygen(s)" relates to any saturated or unsaturated 5 to 7 membered heteroring containing one or two oxygen(s). In a preferred embodiment the heteroring is saturated and stands for 1,3-dioxolane.

In preferred embodiments the 5-7- and 5-8-membered heterorings contain 2 heteroatoms, more preferably selected from N and O.

The definition of "phenylene group" means 1,2-phenylene group, 1,3-phenylene group or 1,4-phenylene group, preferably 1,2-phenylene group The more preferred embodiments of the substituents and above general phrases are given in the examples.

The compounds of general formula (I) have at least one double bond (since there is a double bond in the oxime moiety, but further double bond can be present in an optional substituent, too). The invention relates to all possible E- and Z-isomers of compounds of general formula (I), with respect to every double bond being in the molecule, and to any mixtures of these isomers. In one preferred embodiment, the compounds of formula (I) are in the E configuration of the double bond of the oxime moiety. In another preferred embodiment, the compounds of formula (I) are in the Z configuration of the double bond of the oxime moiety. The compounds of general formula (I) may also have further stereoisomers, due, e.g., to the presence of stereogenic centers. The invention relates to all possible stereoisomers.

The invention also includes all solvates of the compounds referred to in the above formulas, including all hydrates of the compounds referred to in the above formulas. The invention also includes all polymorphs, including crystalline and non-crystalline forms of the compounds referred to in the above formulas. The invention also includes all salts of the compounds referred to in the above formulas, particularly pharmaceutically-acceptable salts. In all uses of the compounds of the above formulas disclosed herein, the invention also includes use of any or all of the stereochemical, E or Z forms, solvates, hydrates, polymorphic, crystalline, non-crystalline, salt, pharmaceutically acceptable salt variations of the compounds described.

If the stereochemistry is not indicated explicitly in a chemical structure or a chemical name, the chemical structure or chemical name is intended to embrace all possible stereoisomers of the given compound.

Pharmaceutical compositions suitable for use include compositions wherein the active ingredients are contained in an effective amount to achieve their intended purpose. A therapeutically effective amount means an amount effective to prevent development of a disease or to alleviate the existing symptoms of the subject being treated. Determination of the effective amounts is well within the capability of those skilled in the art.

For all of the compositions and methods using the compounds of the invention, the compounds according to the invention can be admixed with one or more non-toxic, pharmaceutically acceptable auxiliaries as carriers and/or diluents and/or adjuvants and/or other active ingredients. The carrier can be any of those conventionally used and is limited only by chemico-physical considerations, such as the solubility and lack of the reactivity of the compound, and by the route of administration. Pharmaceutical compositions can be prepared by methods and contain excipients which are well known in the art. A generally recognized compendium of such methods and ingredients is Remington's Pharmaceutical Sciences.

According to the invention the SSAO/VAP-1 related diseases may be: diseases or disorders related to an elevated level of SSAO/VAP-1 (where the elevated level may affect the binding function, amine oxidase function, or both), including but not limited to acute or chronic inflammatory conditions and diseases, connective tissue inflammatory conditions and diseases, rheumatoid arthritis, ankylosing spondylitis, osteoarthritis, lupus erythematosus, vasculitis, synovitis, gastrointestinal inflammatory conditions and diseases, ulcerative colitis, Crohn's disease, irritable bowel syndrome, central nervous system inflammatory conditions and diseases, Alzheimer's disease, multiple sclerosis, chronic multiple sclerosis, pulmonary inflammatory conditions and diseases, asthma, inflammatory skin conditions, psoriasis, atopic eczema, contact dermatitis, atopic dermatitis, liver inflammatory conditions and diseases, inflammatory eye conditions, uveitis, conjunctivitis, corneal angiogenesis, age-related macular degeneration, diseases related to carbohydrate metabolism, type I and/or type II diabetes, complications of diabetes, vascular complications and/or neuropathy and/or retinopathy and/or nephropathy related to diabetes, diabetic retinopathy and macular oedema, diseases related to adipocyte dysfunction, diseases related to smooth muscle cell dysfunction, atherosclerosis, obesity, vascular diseases, ischemic heart disease, arteriosclerosis, Raynaud's disease, stroke and/or complications thereof, cancer or cancer metastasis.

A compound of formula (I) can be administered per se in a therapeutically effective amount, or with one or more additional compounds of formula I. When administered in combination, the compounds can either be administered in amounts that would be therapeutically effective were the compounds to be administered per se, or in amounts that would not be therapeutically effective were the compounds to be administered per se, but which are therapeutically effective in combination. One or more compounds of formula (I) can also be administered with other compounds exhibiting therapeutically useful effect not included in formula I; the compounds can either be administered in amounts that would be therapeutically effective were the compounds to be administered per se, or in amounts that would not be therapeutically effective were the compounds to be administered per se, but which are therapeutically effective in combination.

The method of the present invention can involve the co-administration of other pharmaceutically active compound(s), co-administration meaning administration of other pharmaceutically active compound(s) before, concurrently with, e.g., in combination with an SSAO/VAP-1 inhibitor in the same formulation or in separate formulations, or after administration of the SSAO/VAP-1 inhibitor. Other pharmaceutically active compounds can be corticosteroids and non-corticosteroidal anti-inflammatory compounds. Further compounds to be co-administered can be vitamins, minerals, antioxidants and micronutrients.

The pharmaceutical compositions of the present invention can be administered to humans and any animal that can experience the beneficial effects of the compounds of the invention. Foremost among them are humans, although the invention is not intended to be so limited.

The pharmaceutical compositions of the present invention can be administered by any means that achieve their intended purpose. The mode of administration can be selected to maximize delivery to a desired target site in the body. Routes of administration of the compounds of the present invention can be, for example, parenteral, subcutaneous, intravenous, intraarticular, intrathecal, intramuscular, intraperitoneal, intradermal, intramuscular, subconjunctival, parabulbar, retrobulbar, subtenon, intracameral, intravitreal and other injections, transdermal, buccal, oromucosal, ocular, via inhalation or oral. The manner in which the SSAO/VAP-1 inhibitor is administered is dependent, in part, upon whether the treatment of an SSAO/VAP-1 associated disease is prophylactic or therapeutic.

The dosage administered will be dependent upon a variety of factors, including the strength of the particular SSAO/VAP-1 inhibitor to be employed, species, the age, health, weight of the recipient, kind of concurrent treatment, if any, frequency of treatment, degree of the SSAO/VAP-1 associated disease and the nature of the effect desired. The exact formulation, route of administration and dosage can be chosen by the individual physician in view of the patient's condition. The desired dose may be presented in single dose or as divided doses administered at appropriate intervals.

The "prevention or treatment of diseases related to elevated levels of SSAO/VAP-1" or "prevention or treatment of SSAO/VAP-1 related disease" is intended to include administration of a compound having SSAO/VAP-1 inhibitory activity (i.e. SSAO/VAP-1 inhibitor) to a subject for therapeutic purposes, which may include propylaxis, amelioration, prevention and cure of the above described SSAO/VAP-1 related disease. As used herein, by the term "subject" is meant a target of the administration of SSAO/VAP-1 inhibitor in the present invention, such as mammal, especially human. The therapeutic method comprises administration of an SSAO/VAP-1 inhibitor in an amount sufficient to treat the SSAO/VAP-1 related disease. Any SSAO/VAP-1 inhibitor can be used in the method of the present invention as long as it is safe and effective.

Of course, in the above detailed compounds of general formula (I'), use, pharmaceutical compositions, method of prevention and treatment it is advisable to apply the above-discussed preferred compounds of general formula (I).

Compounds for use in the invention can be assayed for SSAO/VAP-1 inhibitory activity by the protocol in the examples below.

Synthetic Methods

The compounds of the present invention may be prepared according to known methods with use of starting materials that are commercially available or can be prepared following known procedures.

Compounds of the general formula Ar—(CH$_2$)$_n$—CR$^1$=N—OR$^2$ are prepared in accordance with, but not limited to, the following procedures.

Procedure A

A method of synthesizing the appropriate oximes (Scheme 1) which can be adapted for the synthesis of the compounds covered in the present invention is based on conditions well known in the art by reacting the aldehydes with (O-alkyl) hydroxylamine hydrochloride in the presence of e.g. sodium acetate in e.g. ethanol/water at room temperature/under reflux. Products thus obtained can be isolated or purified by known separation or purification methods, such as concentration in vacuo, solvent extraction, crystallization, recrystallization, chromatography and the like.

Scheme 1

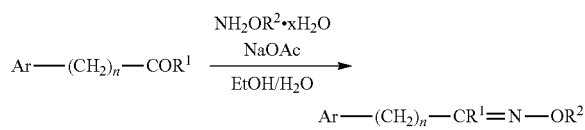

Some of the methods used for the synthesis of starting aldehydes not commercially available are exemplified in the procedures below. The reactions given below are made with preferred starting compounds and preferred reagents, among preferred reaction conditions. Compounds being similar to the products of the reaction schemes (i.e. structural analogues) can be prepared by the choice of the corresponding starting materials, reagents and reaction conditions. Such modification of the reactions given above and below to prepare the desired structural analogues is within the knowledge of a person skilled in synthetic organic chemistry.

Procedure B

The appropriate pen substituted naphtaldehydes can be synthesized from the corresponding amine as exemplified in the synthesis of 8-pyrrolidino-1-naphthaldehyde, which is shown below in Scheme 2:

Scheme 2

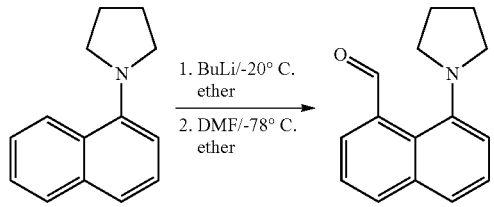

A solution of 1-(1-naphthyl)pyrrolidine in ether was cooled and treated stepwise with n-butyllithium and N,N-dimethylformamide to afford the aldehyde.

Procedure C

Benzodioxole aldehydes can be synthesized by one of the methods exemplified below.

A method for synthesizing 5-alkoxy derivatives of 1,3-benzodioxole-4-carbaldehyde from the corresponding alcohol is exemplified in the synthesis of 5-ethoxy-1,3-benzodioxole-4-carbaldehyde, which is shown below in Scheme 3:

Scheme 3

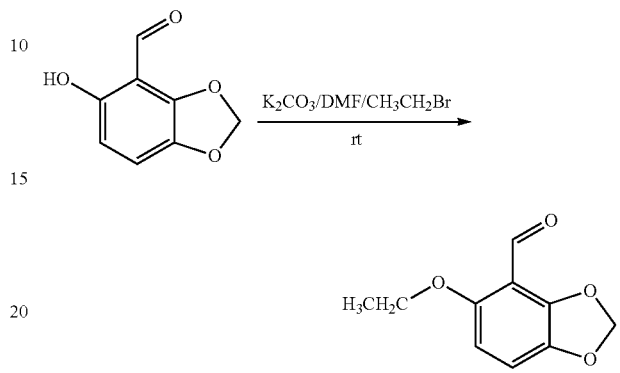

A solution of 5-hydroxy-1,3-benzodioxole-4-carbaldehyde and K$_2$CO$_3$ in N,N-dimethylformamide was treated with ethyl-bromide at room temperature to provide the corresponding 5-ethoxy derivative.

A method of synthesizing 1,3-benzodioxole-4-carbaldehyde compounds having a 2-substituted phenyl substituent at 5 position is exemplified in the synthesis of 5-(2-formylphenyl)-1,3-benzodioxole-4-carbaldehyde shown in Scheme 4:

Scheme 4

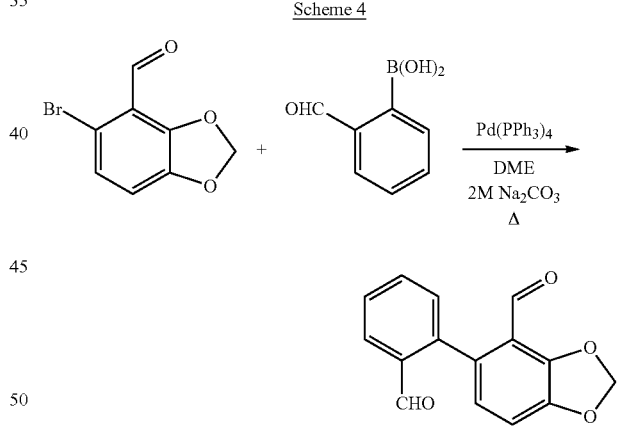

Suzuki reaction of 5-bromo-1,3-benzodioxole-4-carbaldehyde with 2-formylphenylboronic acid in dimethoxyethane, using Pd(PPh$_3$)$_4$ as catalyst and 2M Na$_2$CO$_3$ as base afforded the appropriate 5-(2-formylphenyl) product.

Procedure D

Synthesis of 1,3-dimethyl-2,4-dioxo-1,2,3,4-tetrahydropyrimidine carbaldehydes is exemplified in the methods below.

A method for the synthesis of O-alkyl derivatives of 6-chloro-1,3-dimethyl-2,4-dioxo-1,2,3,4-tetrahydropyrimidine-5-carbaldehyde is exemplified in the synthesis of 6-methoxy-1,3-dimethyl-2,4-dioxo-1,2,3,4-tetrahydropyrimidine-5-carbaldehyde, which is shown in Scheme 5:

Scheme 5

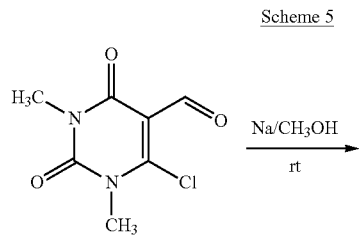

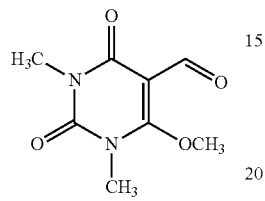

Carbaldehyde was added to a stirred solution of sodium in dry alcohol to afford the appropriate alkoxycarbaldehyde derivative.

A method for the synthesis of S-alkyl or S-aryl derivatives of 6-chloro-1,3-dimethyl-2,4-dioxo-1,2,3,4-tetrahydropyrimidine-5-carbaldehyde is exemplified in the synthesis of 6-(ethylthio)-1,3-dimethyl-2,4-dioxo-1,2,3,4-tetrahydropyrimidine-5-carbaldehyde, which is shown in Scheme 6:

Scheme 6

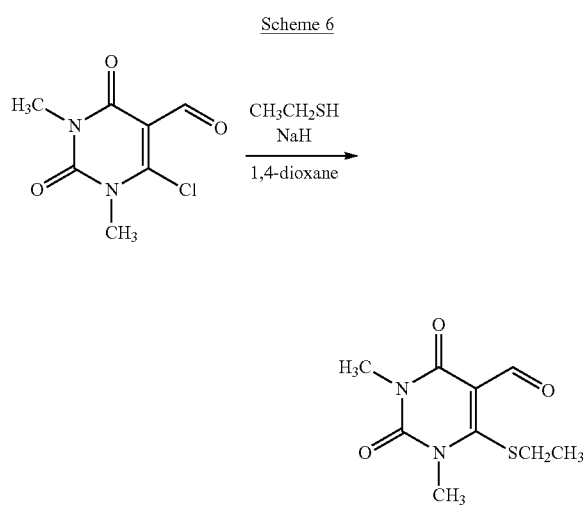

6-Chloro-1,3-dimethyl-2,4-dioxo-1,2,3,4-tetrahydropyrimidine-5-carbaldehyde was added to a stirred solution of ethanethiol in 1,4-dioxane and sodium hydride while cooling the mixture and stirred at room temperature to afford the appropriate 6-ethylthio derivative.

Derivatives substituted with a N-containing cycle at position 6 can be synthesized by the method exemplified by the synthesis of 1,3-dimethyl-2,4-dioxo-6-(4-phenylpiperazin-1-yl)-1,2,3,4-tetrahydropyrimidine-5-carbaldehyde, which is shown in Scheme 7:

Scheme 7

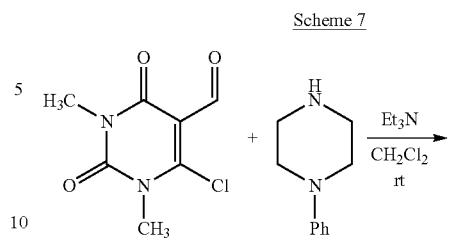

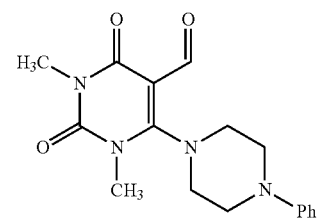

A solution of the carbaldehyde in dichloromethane in the presence of triethylamine was cooled and treated with N-phenylpiperazine to afford the appropriate 6-(4-phenylpiperazin-1-yl) derivative.

Procedure E

Pyridazinone carbaldehydes can be synthesized by one of the methods exemplified below.

Derivatives substituted with a N-containing cycle at position 5 can be synthesized by the method exemplified by the synthesis of 2-methyl-5-(4-methylpiperazino)-3-oxo-2,3-dihydropyridazine-4-carbaldehyde, which is shown in Scheme 8:

Scheme 8

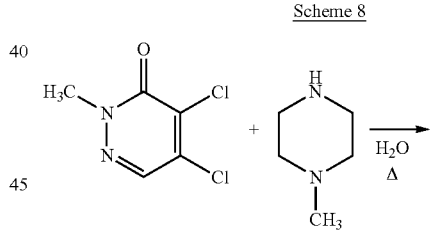

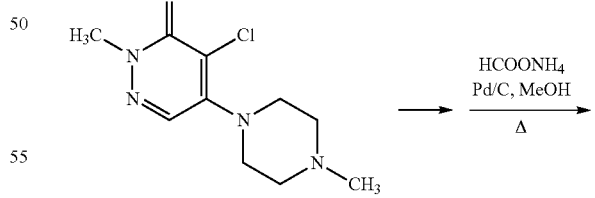

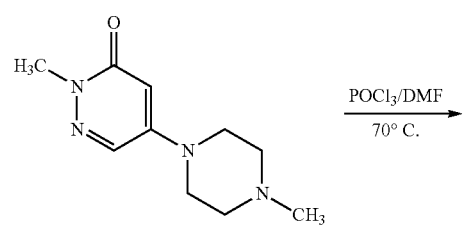

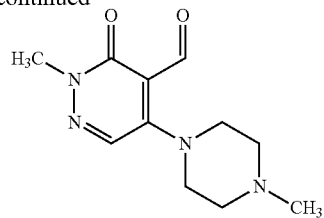

The title product was obtained starting from 4,5-dichloro-2-methylpyridazin-3(2H)-one in 3 steps, first by treating it with 1-methylpiperazine in water under reflux, in the second step by removal of the 4-chloro substituent by treatment with ammonium formate in methanol in the presence of Pd/C, and in the last step by Vilsmeier formylation.

Pyridazino benzaldehydes can be synthesized by the method exemplified in the synthesis of 2-[5-(dimethylamino)-2-methyl-3-oxo-2,3-dihydropyridazin-4-yl]benzaldehyde, which is shown in Scheme 9:

Scheme 9

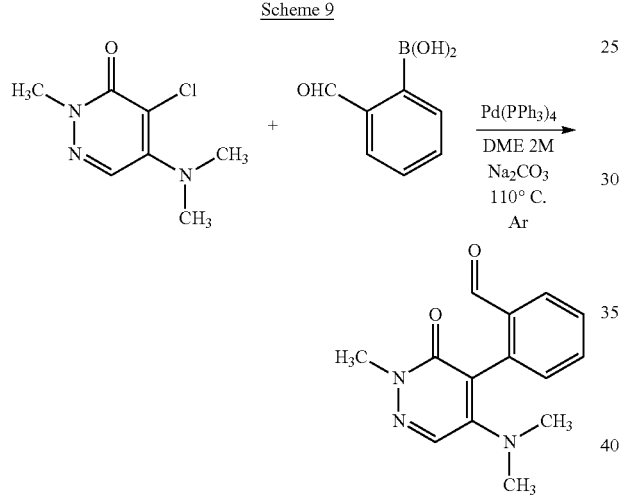

Suzuki reaction of 4-chloro-5-(dimethylamino)-2-methylpyridazin-3(2H)-one with 2-formylphenylboronic acid in dimethoxyethane, using Pd(PPh$_3$)$_4$ as catalyst and 2M Na$_2$CO$_3$ as base afforded the title compound.

The following examples are provided for the purpose of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

EXAMPLES

All melting points were determined on a Büchi apparatus or on a Kofler hot-stage microscope and are uncorrected. The $^1$H NMR spectra were recorded at ambient temperature in the solvent indicated, using the $^2$H signal of the solvent as the lock and tetramethylsilane or the residual undeuterated solvent as the internal standard. Chemical shifts (δ) are given in parts per million and all coupling constants (J) in hertz. Varian Mercury Plus spectrometer at 400 MHz or a Varian Unity Plus spectrometer at 300 MHz were used. Flash column chromatography was performed on Kieselgel 60 (Merck, 0.040-0.063 mm). The elemental analyses have been carried out with an Elementar Vario EL III apparatus. For TLC analysis Silica gel 60 F$_{254}$ (Merck) plates were applied. Solvent mixtures used for chromatography are always given in a vol/vol ratio. The reagents were obtained from commercial sources and used as received. Solvents were dried and distilled prior to use.

The synthesis of the compounds are depicted in Schemes 1-9 above, as well as in the following examples, which are not to be construed as limitative.

I. Type 1 of Production Examples

Synthesis of Benzaldehyde Oximes (Procedure A)

1.1: Example 1

3-Methoxy-2-methylbenzaldehyde oxime (compound 1)

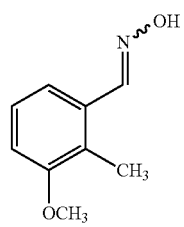

Step 1: 3-Methoxy-2-methylbenzaldehyde

The preparation of 3-methoxy-2-methylbenzaldehyde starting from m-anisaldehyde is described by Comins D. L. et al., *J. Org. Chem.*, 54(15), 3730 (1989).

Yield: 0.390 g (44%), pale yellow oil.

$^1$H NMR (CDCl$_3$): 2.54 (s, 3H, Ar—CH$_3$); 3.90 (s, 3H, O—CH$_3$); 7.08 (dd, 1H, Ar); 7.31 (t, 1H, Ar); 7.43 (dd, 1H, Ar); 10.32 (s, 1H, CHO).

Step 2: 3-Methoxy-2-methylbenzaldehyde oxime (Method A, as a preferred embodiment of Procedure A, Scheme 1) (compound 1)

To an ice-cooled and stirred suspension of 3-methoxy-2-methylbenzaldehyde (0.269 g, 1.8 mmol) in ethanol (15 ml) a solution of NaOAc.3H$_2$O (1.3 eq) and NH$_2$OH.HCl (1.3 eq) in water (5 ml) was added dropwise within 5 minutes. The resulting suspension was stirred at room temperature until the starting material was consumed (monitored by TLC). After evaporation of the ethanol in vacuo, water was added to the residue. Then the precipitated crystals were filtered off. The crude product was purified by column chromatography with a mixture of chloroform:ethyl acetate (95:5) as the eluent.

Yield: 0.218 g (74%), white crystals. Mp.: 110° C.

$^1$H NMR (CDCl$_3$): 2.29 (s, 3H, Ar—CH$_3$); 3.84 (s, 3H, N—CH$_3$); 6.88 (d, 1H, Ar); 7.18 (t, 1H, Ar); 7.30 (d, 1H, Ar); 8.42 (s, 1H, CH); 8.47 (s, 1H, N—OH).

Analysis calculated for $C_9H_{11}NO_2$ (165.19): C, 65.44%; H, 6.71%; N, 8.48%. Found: C, 65.45%; H, 6.64%; N, 8.45%.

I.2: Example 2

1-[2-(Allyloxy)-4-bromophenyl]ethanone oxime (compound 2)

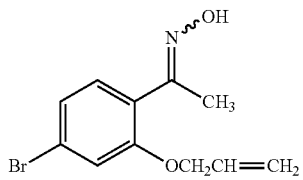

The process described in Method A was followed. 1-[2-(Allyloxy)-4-bromophenyl]ethanone (0.088 g, 0.34 mmol, see in Bioorg. Med. Chem., 2007, 15(12), 4048-4056) was used to obtain the title compound.

Work-up/purification: after evaporation of the ethanol in vacuo, water was added to the residue. Then the precipitated crystals were filtered off and washed with water and n-pentane.

Yield: 0.074 g (79%), white crystals. Mp.: 115° C.

$^1$H NMR (DMSO-$d_6$): 2.05 (s, 3H, $CH_3$); 4.65 (d, 2H, O—$CH_2$); 5.27 and 5.37 (dd, 2H, =$CH_2$); 6.02 (m, 1H, CH); 7.15 (m, 2H, Ar); 7.25 (m, 1H, Ar); 11.13 (s, 1H, N—OH).

Analysis calculated for $C_{11}H_{12}BrNO_2$ (270.12): C, 48.91%; H, 4.48%; N, 5.19%. Found: C, 48.44%; H, 4.22%; N, 5.11%.

I.3: Example 3

1-[2-(Allyloxy)-5-bromophenyl]ethanone oxime (compound 3)

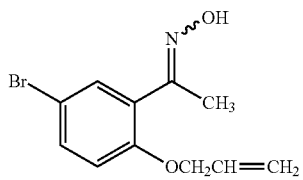

The process described in Method A was followed. 1-[2-(Allyloxy)-5-bromophenyl]ethanone (0.090 g, 0.35 mmol, see in Bioorg. Med. Chem., 2007, 15(12), 4048-4056) was used to obtain the title compound.

Work-up/purification: after evaporation of the ethanol in vacuo, water was added to the residue. Then the precipitated crystals were filtered off and washed with water and n-pentane.

Yield: 0.082 g (87%), white crystals. Mp.: 110-111° C.

$^1$H NMR (DMSO-$d_6$): 2.06 (s, 3H, $CH_3$); 4.61 (d, 2H, O—$CH_2$); 5.26 and 5.37 (dd, 2H, =$CH_2$); 6.02 (m, 1H, CH); 7.03 (d, 1H, Ar); 7.32 (d, 1H, Ar); 7.50 (dd, 1H, Ar); 11.18 (s, 1H, N—OH).

Analysis calculated for $C_{11}H_{12}BrNO_2$ (270.12): C, 48.91%; H, 4.48%; N, 5.19%. Found: C, 48.81%; H, 4.16%; N, 5.13%.

I.4: Example 4

2-[(2-Phenylprop-2-en-1-yl)oxy]benzaldehyde oxime (compound 4)

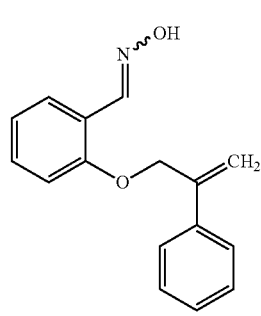 [SMILES: C=C(COc1ccccc1C=NO)c1ccccc1]

Step 1:
2-[(2-Phenylprop-2-en-1-yl)oxy]benzaldehyde

A suspension of 0.763 g (6.25 mmol) 2-hydroxybenzaldehyde, 1.009 g (5.12 mmol) [1-(bromomethyl)vinyl]benzene and 0.850 g (6.15 mmol) $K_2CO_3$ in 20 ml acetone was stirred at room temperature for 48 h. After evaporation to dryness, 20 ml water and 20 ml dichloromethane was added to the residue. After separation of the phases, the aqueous phase was extracted with a further 2×20 ml of dichloromethane and the combined organic phases were dried over $MgSO_4$ and evaporated to dryness. The crude product obtained was purified by column chromatography with chloroform as the eluent.

Yield: 0.102 g (8%), pale yellow oil.

$^1$H NMR ($CDCl_3$): 5.02 (t, 2H, $OCH_2$, J=0.9); 5.48 and 5.63 (q, 1H, =$CH_2$, $J_1$=$J_2$=0.9); 7.00-7.86 (m, 9H, Ar); 10.39 (s, 1H, CHO).

Step 2:
2-[(2-Phenylprop-2-en-1-yl)oxy]benzaldehyde oxime (compound 4)

The process described in Method A was followed. 2-[(2-Phenylprop-2-en-1-yl)oxy]benzaldehyde (0.102 g, 0.43 mmol) was used to obtain the title compound.

Work-up/purification: after evaporation of the ethanol in vacuo, water was added to the residue. The aqueous phase was extracted with dichloromethane. The combined organic phases were dried over $MgSO_4$ and evaporated to dryness. The crude product was purified by column chromatography with a mixture of chloroform:ethyl acetate (1:1) as the eluent.

Yield: 0.09 g (83%), white crystals. Mp.: 61-62° C.

¹H NMR (CDCl₃): 9.95 (bs, 2H, OCH₂); 5.45 and 5.60 (bs, 1H, =CH₂); 6.92-7.76 (m, 9H, Ar); 8.24 (s, 1H, NOH); 8.45 (s, 1H, CHN).

II. Type 2 of Production Examples

Synthesis of Naphtaldehyde Oximes (Procedure B)

II.1: Example 5

8-Pyrrolidino-1-naphtaldehyde oxime (compound 5)

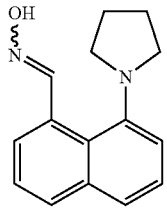 [SMILES: ON=Cc1cccc2cccc(N3CCCC3)c12]

Step 1: 8-Pyrrolidino-1-naphtaldehyde n-Butyllithium (14.7 ml of a 1.7 M solution in hexane) was added dropwise to a stirred solution of 1-(1-naphthyl)pyrrolidine (25.00 mmol, 5.00 g) in dry ether (50 ml) at −20° C. under argon. After 48 hours a solution of dry N,N-dimethylformamide (6.2 ml, 75.00 mmol) in ether (10 ml) was added dropwise at −78° C. to the reaction mixture. The mixture was allowed to warm to −20° C. over 4 hours, then quenched with a solution of methanol (15 ml) and allowed to warm to room temperature. The reaction mixture was diluted with ether (100 ml), washed with water (3×150 ml) and with brine (150 ml), dried over MgSO₄ and evaporated under reduced pressure. The residue was purified by column chromatography using dichloromethane as eluent to afford the aldehyde which was crystallized from hexane.

Yield: 3.54 g (63%), yellow crystals. Mp.: 44.1-44.5° C.

¹H NMR (CDCl₃): 1.96 (s, 4H, H-3, H-4 pyrrolidine); 2.65-3.45 (br, 4H, H-2, H-5 pyrrolidine); 7.32 (d, 1H, H-7 Ar, J=7.4); 7.42-7.58 (m, 3H, H-3, H-5, H-6 Ar); 7.62 (d, 1H, H-4 Ar, J=8.2); 7.88 (d, 1H, H-2 Ar, J=8.2); 10.63 (s, 1H, CHO).

Analysis calculated for $C_{16}H_{13}N_3$ (225.28): C, 79.97%; H, 6.71%; N, 6.22%. Found: C, 79.77%; H, 6.72%, N, 6.14%.

Step 2: 8-Pyrrolidino-1-naphthaldehyde oxime (compound 5)

The process described in Method A was followed. 8-Pyrrolidin-1-yl-1-naphthaldehyde (0.500 g, 2.20 mmol) was used to obtain the title compound.

Work-up/purification: the precipitated product was filtered off and washed with water and ethanol. The crude product was purified by crystallization from 95% ethanol.

Yield: 0.344 g (65%), yellow crystals. Mp.: 187.4-188.5° C.

¹H NMR (DMSO-d₆): 1.88 (bs, 4H, CH₂—CH₂ pyrrolidine); 2.70 and 3.24 (bs, 2H and bs, 2H, N(CH₂)₂ pyrrolidine); 7.21-7.23 (m, 1H, H-7); 7.39-7.47 (m, 2H, H-2, H-6); 7.56-7.60 (m, 2H, H-3, H-5); 7.86-7.88 (m, 1H, H-4); 9.08 (s, 1H, HO—N=C—H); 10.81 (1H, s, OH).

Analysis calculated for $C_{15}H_{16}N_2O$ (240.30): C, 74.97%; H, 6.71%; N, 11.66%. Found: C, 75.09%; H, 6.66%; N, 11.49%.

III. Type 3 of Production Examples

Synthesis of Benzodioxole Oximes (Procedure C)

III.1: Example 6

5-Hydroxy-1,3-benzodioxole-4-carbaldehyde oxime (compound 6)

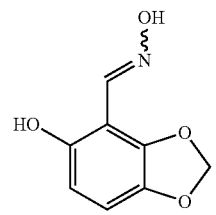 [SMILES: ON=Cc1c(O)ccc2c1OCO2]

Step 1: 5-Hydroxy-1,3-benzodioxole-4-carbaldehyde

The preparation of 5-hydroxy-1,3-benzodioxole-4-carbaldehyde starting from 1,3-benzodioxol-5-ol is described by Birch A. M. et al., WO1998/9840386.

Yield: 1.00 g (56%), pale yellow crystals. Mp.: 112-115° C.

¹H NMR (CDCl₃): 6.07 (s, 2H, O—CH₂—O); 6.37 (d, 1H, Ar); 6.97 (d, 1H, Ar); 10.14 (s, 1H, Ar—OH); 10.42 (s, 1H, CHO).

Analysis calculated for $C_8H_6O_4$ (166.13): C, 57.84%; H, 3.64%. Found: C, 57.88%; H, 3.39%.

Step 2: 5-Hydroxy-1,3-benzodioxole-4-carbaldehyde oxime (compound 6)

The process described in Method A was followed. 5-Hydroxy-1,3-benzodioxole-4-carbaldehyde (0.249 g, 1.50 mmol) was used to obtain the title compound.

Work-up/purification: after evaporation of ethanol in vacuo, water was added to the residue. Then the precipitated crystals were filtered off and washed with water and n-pentane.

Yield: 0.231 g (88%), pale yellow crystals. Mp.: 161-162° C.

¹H NMR (DMSO-d₆): 5.97 (s, 2H, O—CH₂—O); 6.29 (d, 1H, Ar); 6.75 (d, 1H, Ar); 8.18 (s, 1H, CH); 9.60 (s, 1H, Ar—OH); 11.45 (s, 1H, N—OH).

Analysis calculated for $C_8H_7NO_4$ (181.15): C, 53.04%; H, 3.89%; N, 7.73%. Found: C, 53.09%; H, 3.80%; N, 7.78%.

III.2: Example 7

5-Ethoxy-1,3-benzodioxole-4-carbaldehyde oxime (compound 7)

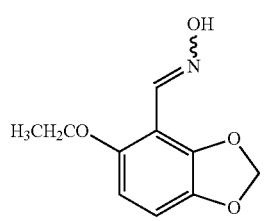

Step 1: 5-Ethoxy-1,3-benzodioxole-4-carbaldehyde

Under argon to a stirred solution of 5-hydroxy-1,3-benzodioxole-4-carbaldehyde (0.151 g, 0.91 mmol) and $K_2CO_3$ (1 eq) in dry N,N-dimethylformamide (2 ml) ethyl-bromide (1 eq) was added. The mixture was stirred at room temperature for 18 h until the starting material had been consumed (monitored by TLC). Then the mixture was poured onto ice water (15 ml). This aqueous phase was extracted with ethyl acetate (1×40 ml, then 2×15 ml) and the combined organic phases were washed with water and dried over anhydrous $MgSO_4$. The solvent was evaporated in vacuo, and the crude product was purified by column chromatography with a mixture of n-hexane:ethyl acetate (4:1) as the eluent.

Yield: 0.071 g (40%), pale yellow crystals. Mp.: 155-156° C.

$^1$H NMR (CDCl$_3$): 1.44 (t, 3H, CH$_3$); 4.06 (q, 2H, O—CH$_2$); 6.08 (s, 2H, O—CH$_2$—O); 6.32 (d, 1H, Ar); 6.89 (d, 1H, Ar); 10.40 (s, 1H, CHO).

Analysis calculated for $C_{10}H_{10}O_4$ (194.18): C, 61.85%; H, 5.19%. Found: C, 61.61%; H, 5.49%.

Step 2: 5-Ethoxy-1,3-benzodioxole-4-carbaldehyde oxime (compound 7)

The process described in Method A was followed. 5-Ethoxy-1,3-benzodioxole-4-carbaldehyde (0.090 mg, 0.46 mmol) was used to obtain the title compound.

Work-up/purification: after evaporation of ethanol in vacuo, water was added to the residue. Then the precipitated crystals were filtered off and washed with water and n-pentane.

Yield: 0.075 g (77%), yellow crystals. Mp.: 161-164° C.

$^1$H NMR (CDCl$_3$): 1.40 (t, 3H, CH$_3$); 3.98 (q, 2H, O—CH$_2$); 6.04 (s, 2H, O—CH$_2$—O); 6.31 (d, 1H, Ar); 6.73 (d, 1H, Ar); 8.47 (s, 1H, CH); 9.62 (s, 1H, N—OH).

Analysis calculated for $C_{10}H_{11}NO_4$ (209.19): C, 57.41%; H, 5.30%; N, 6.70%. Found: C, 57.30%; H, 4.93%; N, 6.69%.

III.3: Example 8

5-(Allyloxy)-1,3-benzodioxole-4-carbaldehyde oxime (compound 8)

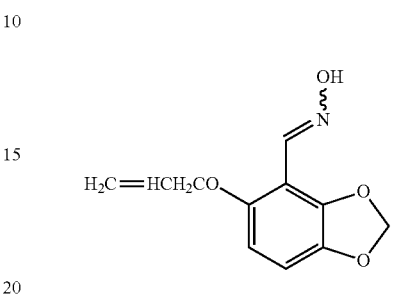

Step 1: 5-(Allyloxy)-1,3-benzodioxole-4-carbaldehyde

To a stirred solution of 5-hydroxy-1,3-benzodioxole-4-carbaldehyde (0.166 g, 1.00 mmol) and $K_2CO_3$ (1.00 mmol) in dry N,N-dimethylformamide (2 ml) was added allylbromide (1.00 mmol) under argon. The mixture was stirred at room temperature for 18 h until the starting material was consumed (monitored by TLC). Then the mixture was poured onto ice-water (15 ml). The aqueous phase was filtered off, the precipitated product was washed with water and n-heptane and dried to give analytically pure crystals.

Yield: 0.148 g (80%), pale yellow crystals. Mp.: 102-103° C.

$^1$H NMR (CDCl$_3$): 4.57 (dt, 2H, OCH$_2$); 5.32 (dq, 1H, =CH$_2$ cis); 5.43 (dq, 1H, =CH$_2$ trans); 6.06 (ddt, 1H, CH); 6.10 (s, 2H, OCH$_2$O); 6.34 (d, 1H, Ar); 6.90 (d, 1H, Ar); 10.42 (s, 1H, CHO).

Analysis calculated for $C_{11}H_{10}O_4$ (206.19): C, 64.07%; H, 4.89%. Found: C, 64.20%; H, 5.23%.

Step 2: 5-(Allyloxy)-1,3-benzodioxole-4-carbaldehyde oxime (compound 8)

The process described in Method A was followed. 5-(Allyloxy)-1,3-benzodioxole-4-carbaldehyde (0.090 mg, 0.43 mmol) was used to obtain the title compound.

Work-up/purification: after evaporation of ethanol in vacuo, water was added to the residue. Then the precipitated crystals were filtered off. The crude product was purified by column chromatography with a mixture of n-hexane:ethyl acetate (2:1) as the eluent.

Yield: 0.078 g (81%), yellow crystals. Mp.: 166-167° C.

$^1$H NMR (CDCl$_3$): 4.50 (dt, 2H, OCH$_2$); 5.29 (dq, 1H, =CH$_2$ cis); 5.40 (dq, 1H, =CH$_2$ trans); 6.03 (ddt, 1H, CH); 6.05 (s, 2H, OCH$_2$O); 6.33 (d, 1H, Ar); 6.73 (d, 1H, Ar); 8.49 (s, 1H, NCH); 9.60 (s, 1H, N—OH).

Analysis calculated for $C_{11}H_{11}NO_4$ (221.21): C, 59.73%; H, 5.01%; N, 6.33%. Found: C, 59.80%; H, 4.78%; N, 6.21%.

III.4: Example 9

5-Bromo-1,3-benzodioxole-4-carbaldehyde oxime (compound 9)

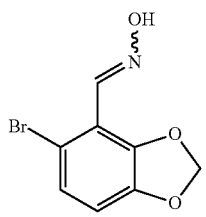 [SMILES: ON=Cc1c(Br)ccc2c1OCO2]

The process described in Method A was followed. 5-Bromo-1,3-benzodioxole-4-carbaldehyde (2.00 g, 8.50 mmol, commercially available, e.g. from Aldrich) was used to obtain the title compound.

Work-up/purification: after evaporation of ethanol in vacuo, water was added to the residue. Then the precipitated crystals were filtered off and washed with water.

Yield: 2.02 g (95%), white crystals. Mp.: 239-240° C.

$^1$H NMR (DMSO-$d_6$): 6.13 (s, 2H, OCH$_2$O); 6.90 and 7.15 (d, 2H, aromatic protons, J=8.2); 8.18 (s, 1H, CHN); 11.73 (s, 1H, NOH).

Analysis calculated for $C_8H_6BrNO_3$ (244.04): C, 39.37%; H, 2.48%; N, 5.74%. Found: C, 39.37%; H, 2.25%; N, 5.65%.

III.5: Example 10

5-Bromo-2-methyl-1,3-benzodioxole-4-carbaldehyde oxime (compound 10)

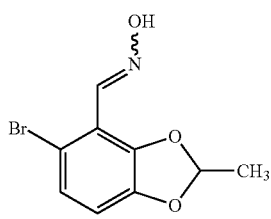

Step 1: (R,S)-5-Bromo-2-methyl-1,3-benzodioxole

The preparation of 5-bromo-2-methyl-1,3-benzodioxole starting from catechol is described by Lynch G. S. et al., WO1994/9402475.

5-Bromo-2-methyl-1,3-benzodioxole-4-carbaldehyde

The (R,S)-5-bromo-2-methyl-1,3-benzodioxole (5.00 g, 23.25 mmol) was added dropwise under argon to a −78° C. stirred solution of lithium diisopropylamide (13 ml, 2M in THF/heptane/ethylbenzene) in dry THF (70 ml) at such a rate that the temperature remained below −70° C. The resulting solution was stirred for 15 min at −78° C., and then N,N-dimethylformamide (2.25 ml, 29.06 mmol) was added to the solution. Then it was stirred for 15 min, and the −78° C. cooling bath was removed. The reaction mixture was allowed to warm to room temperature and it was stirred for 30 min at ambient temperature. Then in a small portion water (20 ml) was added to the reaction mixture. The organic phase was separated, washed with 1M HCl (2×50 ml) and with saturated Na$_2$CO$_3$ solution (2×50 ml). The organic layer was dried over anhydrous Na$_2$SO$_4$. The solvent was evaporated in vacuo, and the crude product was purified by crystallization from n-hexane.

Yield: 0.890 g (16%), yellow crystals. Mp.: 81.8-85.1° C.

$^1$H NMR (CDCl$_3$): 1.76 (d, 3H, CH$_3$, J=4.8); 6.47 (q, 1H, H-2); 6.79 (d, 1H, H-7, J=8.4); 7.07 (d, 1H, H-6, J=8.4); 10.28 (s, 1H, CHO).

Analysis calculated for $C_9H_7BrO_3$ (243.05): C, 44.47%; H, 2.90%. Found: C, 44.20%; H, 2.66%.

Step 2: 5-Bromo-2-methyl-1,3-benzodioxole-4-carbaldehyde oxime (compound 10)

The process described in Method A was followed. 5-Bromo-2-methyl-1,3-benzodioxole-4-carbaldehyde (0.500 g, 2.05 mmol) was used to obtain the title compound.

Work-up/purification: after evaporation of ethanol in vacuo, water was added to the residue. Then the precipitated crystals were filtered off. The crude product was purified by crystallization from a mixture of acetone and water (2:1).

Yield: 0.289 g (55%), white crystals. Mp.: 208.0-208.9° C.

$^1$H NMR (DMSO-$d_6$): 1.62 (d, 3H, CH$_3$, J=5.1); 6.47 (q, 1H, H-2); 6.84 (d, 1H, H-7, J=8.4); 7.12 (d, 1H, H-6, J=8.4); 8.18 (s, 1H, HO—N=C—H); 11.77 (1H, s, OH).

Analysis calculated for $C_9H_8BrNO_3$ (258.07): C, 41.89%; H, 3.12%; N, 5.43%. Found: C, 41.37%; H, 2.76%; N, 5.42%.

III.6: Example 11

1-(5-bromo-1,3-benzodioxol-4-yl)-N-[2-(pyrrolidin-1-yl)ethoxy]methanimine (compound 11)

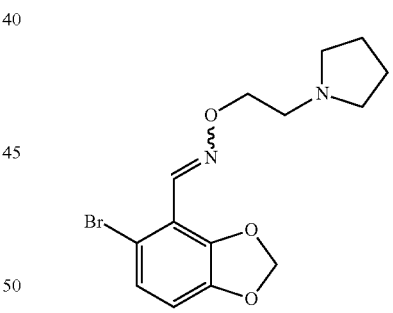

To a stirred solution of 5-bromo-1,3-benzodioxole-4-carbaldehyde oxime (0.244 g, 1 mmol) in dry DMF (15 ml), 1-(2-chloroethyl)pyrrolidine hydrochloride (0.207 g, 1.22 mmol) and NaH (0.138 g, 3.45 mmol, 60% dispersion in oil) were added. The reaction mixture was stirred at ambient temperature for 5 minutes and then heated at 80° C. overnight. Then the reaction mixture was cooled to ambient temperature and quenched with methanol (4 ml). After evaporation of the solvent in vacuo, water (25 ml) was added to the residue, and the mixture was extracted with dichloromethane (2×25 ml). The combined organic phases were dried over anhydrous MgSO$_4$. The solvent was evaporated in vacuo, and the residue was purified by column chromatography with a mixture of chloroform:ethyl acetate (10:1) as the eluent. After the isolation of the unreacted starting material, the eluent was changed to ethyl acetate:isopropanol:cc. NH$_3$ (9:1:0.5). The crude product was digerated with water.

Yield: 0.083 g (24%), brownish white powder. Mp. 68.5-70.0° C.

$^1$H NMR (CDCl$_3$): 1.82 (m, 4H); 2.64 (m, 4H); 2.87 (t, 2H); 4.39 (t, 2H); 6.09 (s, 2H); 6.67 (d, 1H); 7.06 (d, 1H); 8.43 (s, 1H).

Analysis calculated for C$_{14}$H$_{17}$BrN$_2$O$_3$ (341.20): C, 49.28%; H, 5.02%; N, 8.21%. Found: C, 49.16%; H, 4.91%; N, 8.11%.

III.7: Example 12

5-{2-[(hydroxyimino)methyl]phenyl}-1,3-benzo-dioxole-4-carbaldehyde oxime (compound 12)

Step 1:
5-(2-Formylphenyl)-1,3-benzodioxole-4-carbaldehyde (Method B, as a preferred embodiment of Procedure C, Scheme 4)

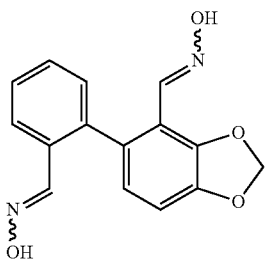 [SMILES: ON=Cc1ccccc1-c1ccc2c(c1C=NO)OCO2]

To a solution of 5-bromo-1,3-benzodioxole-4-carbaldehyde (0.458 g, 2.00 mmol) in dry dimethoxy-ethane were added Pd(PPh$_3$)$_4$ (5 mol %, 0.10 mmol), 2.5 ml 2M Na$_2$CO$_3$ and 2-formylphenylboronic acid (0.450 g, 3.00 mmol) under argon. The reaction mixture was heated under reflux until the starting material was consumed (monitored by TLC). Then the mixture was poured onto ice-water (30 ml) and the aqueous phase was extracted with dichloromethane (3×30 ml). The combined organic phases were dried over anhydrous MgSO$_4$. The solvent was evaporated in vacuo and the crude product was purified by column chromatography with a mixture of hexane:ethyl acetate (9:1) as the eluent.

Yield: 0.400 g (79%), pink crystals. Mp.: 76-78° C.

$^1$H NMR (CDCl$_3$): 6.24 (AB, 2H, CH$_2$, J=1.1); 6.76 (d, 1H, Ar, J=7.8); 7.05 (d, 1H, Ar, J=7.8); 7.31-7.34 (m, 1H, Ar); 7.54-7.59 (m, 1H, Ar); 7.61-7.67 (m, 1H, Ar); 8.00-8.05 (m, 1H, Ar); 9.80 (s, 1H, CHO); 9.90 (s, 1H, CHO).

Analysis calculated for C$_{15}$H$_{10}$O$_4$ (254.24): C, 70.86%; H, 3.96%. Found: C, 70.87%; H, 3.92%.

Step 2: 5-{2-[(Hydroxyimino)methyl]phenyl}-1,3-benzodioxole-4-carbaldehyde oxime (compound 12)

The process described in Method A was followed. 5-(2-Formylphenyl)-1,3-benzodioxole-4-carbaldehyde (0.350 g, 1.38 mmol) was used to obtain the title compound.

Work-up/purification: the reaction mixture was evaporated in vacuo to dryness, to the residue water was added and the aqueous phase was extracted with ethyl acetate. The combined organic phases were dried over anhydrous MgSO$_4$. The solvent was evaporated in vacuo. The crude product was purified by crystallization (two times) from a mixture of ethanol and water (4:1).

Yield: 0.114 g (29%), pink crystals. Mp.: 227-229° C.

$^1$H NMR (DMSO-d$_6$): 6.15+6.17 (AB, 2H, CH$_2$, J=1.0); 6.67 (d, 1H, Ar, J=8.0); 6.99 (d, 1H, Ar, J=8.0); 7.17-7.23 (m, 1H, Ar); 7.40-7.45 (m, 2H, Ar); 7.46 (s, 1H, OH—N=C—H); 7.64 (s, 1H, OH—NH=C—H); 7.83-7.88 (m, 1H, Ar); 11.30 (s, 1H, OH); 11.39 (s, 1H, OH).

Analysis calculated for C$_{15}$H$_{12}$N$_2$O$_4$ (284.27): C, 63.38%; H, 4.25%; N, 9.85%. Found: C, 63.30%; H, 4.14%; N, 9.73%.

III.8: Example 13

5-(2-Fluorophenyl)-1,3-benzodioxole-4-carbaldehyde oxime (compound 13)

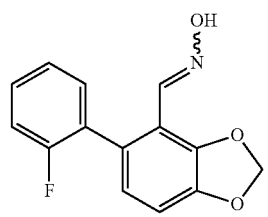 [SMILES: ON=Cc1c(-c2ccccc2F)ccc2c1OCO2]

Step 1:
5-(2-Fluorophenyl)-1,3-benzodioxole-4-carbaldehyde

The process described in Method B was followed. 5-Bromo-1,3-benzodioxole-4-carbaldehyde (0.458 g, 2.00 mmol) and 2-fluorophenylboronic acid (0.420 g, 3.00 mmol) were used to obtain the title compound. The crude product was purified by column chromatography with a mixture of hexane:ethyl acetate (4:1) as the eluent.

Yield: 0.453 g (93%), yellow crystals. Mp.: 84-86° C.

$^1$H NMR (CDCl$_3$): 6.20 (s, 2H, CH$_2$); 6.83 (d, 1H, Ar, J=8.0); 7.05 (d, 1H, Ar, J=8.0); 7.11-7.17 (m, 1H, Ar); 7.20-7.33 (m, 2H, Ar); 7.36-7.43 (m, 1H, Ar); 9.82 (d, 1H, CHO, J=2.9).

Analysis calculated for C$_{14}$H$_9$FO$_3$ (244.22): C, 68.85%; H, 3.71%. Found: C, 68.91%; H, 3.53%.

Step 2:
5-(2-Fluorophenyl)-1,3-benzodioxole-4-carbaldehyde oxime (compound 13)

The process described in Method A was followed. 5-(2-Fluorophenyl)-1,3-benzodioxole-4-carbaldehyde (0.350 g, 1.43 mmol) was used to obtain the title compound.

Work-up/purification: the reaction mixture was evaporated in vacuo to dryness, to the residue water was added and the aqueous phase was extracted with ethyl acetate. The combined organic phases were dried over anhydrous MgSO$_4$. The solvent was evaporated in vacuo. The crude product was purified by crystallization (two times) from a mixture of ethanol and water (4:1).

Yield: 0.180 g (49%), white crystals. Mp.: 197-198° C.

$^1$H NMR (DMSO-d$_6$): 6.15 (s, 2H, CH$_2$); 6.78 (d, 1H, Ar, J=8.0); 7.00 (d, 1H, Ar, J=8.0); 7.24-7.34 (m, 3H, Ar); 7.42-7.49 (m, 1H, Ar); 7.66 (d, 1H, OH—N=C—H, J=2.2); 11.38 (s, 1H, OH).

Analysis calculated for $C_{14}H_{10}FNO_3$ (259.23): C, 64.87%; H, 3.89%; N, 5.40%. Found: C, 64.82%; H, 3.65%; N, 5.34%.

III.9: Example 14

5-(2-Chlorophenyl)-1,3-benzodioxole-4-carbaldehyde oxime (compound 14)

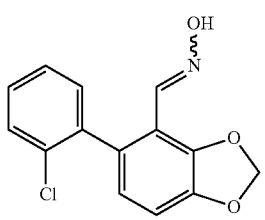

Step 1:
5-(2-Chlorophenyl)-1,3-benzodioxole-4-carbaldehyde

The process described in Method B was followed. 5-Bromo-1,3-benzodioxole-4-carbaldehyde (0.458 g, 2.00 mmol) and 2-chlorophenylboronic acid (0.469 g, 3.00 mmol) were used to obtain the title compound. The crude product was purified by column chromatography with a mixture of hexane:ethyl acetate (4:1) as the eluent.

Yield: 0.420 g (81%), yellow crystals. Mp.: 84-86° C.

$^1$H NMR (CDCl$_3$): 6.20 (AB, 2H, CH$_2$, J=1.2); 6.76 (d, 1H, Ar, J=8.0); 7.04 (d, 1H, Ar, J=8.0); 7.28-7.40 (m, 3H, Ar); 7.44-7.49 (m, 1H, Ar); 9.69 (s, 1H, CHO).

Analysis calculated for $C_{14}H_9ClO_3$ (260.67): C, 64.51%; H, 3.48%. Found: C, 64.37%; H, 3.30%.

Step 2:
5-(2-Chlorophenyl)-1,3-benzodioxole-4-carbaldehyde oxime (compound 14)

The process described in Method A was followed. 5-(2-Chlorophenyl)-1,3-benzodioxole-4-carbaldehyde (0.350 g, 1.34 mmol) was used to obtain the title compound.

Work-up/purification: the reaction mixture was evaporated in vacuo to dryness, to the residue water was added and the aqueous phase was extracted with ethyl acetate. The combined organic phases were dried over anhydrous MgSO$_4$. The solvent was evaporated in vacuo. The crude product was purified by crystallization (two times) from a mixture of ethanol and water (4:1).

Yield: 0.079 g (21%), white crystals. Mp.: 182-183° C.

$^1$H NMR (DMSO-d$_6$): 6.15 (AB, 2H, CH$_2$, J=1.0); 6.69 (d, 1H, Ar, J=7.8); 7.00 (d, 1H, Ar, J=7.8); 7.29-7.33 (m, 1H, Ar); 7.39-7.46 (m, 2H, Ar); 7.51 (s, 1H, OH—N=C—H); 7.53-7.57 (m, 1H, Ar); 11.37 (s, 1H, OH).

Analysis calculated for $C_{14}H_{10}ClNO_3$ (275.69): C, 60.99%; H, 3.66%; N, 5.08%. Found: C, 61.41%; H, 3.42%; N, 5.03%.

III.10: Example 15

5-(2-Bromophenyl)-1,3-benzodioxole-4-carbaldehyde oxime (compound 15)

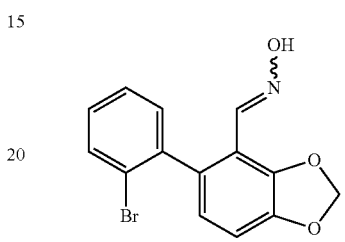

Step 1:
5-(2-Bromophenyl)-1,3-benzodioxole-4-carbaldehyde

The process described in Method B was followed. 5-Bromo-1,3-benzodioxole-4-carbaldehyde (1.15 g, 5.00 mmol) and 2-bromophenylboronic acid (1.10 g, 5.50 mmol) were used to obtain the title compound. The crude product was purified by column chromatography with a mixture of hexane:ethyl acetate (9:1) as the eluent.

Yield: 0.900 g (59%), yellow crystals. Mp.: 89-91° C.

$^1$H NMR (CDCl$_3$): 6.21 (AB, 2H, CH$_2$, J=1.4); 6.73 (d, 1H, Ar, J=8.0); 7.04 (d, 1H, Ar, J=8.0); 7.25-7.33 (m, 2H, Ar); 7.36-7.41 (m, 1H, Ar); 7.63-7.69 (m, 1H); 9.68 (s, 1H, CHO).

Analysis calculated for $C_{14}H_9BrO_3$ (305.12): C, 55.11%; H, 2.97%. Found: C, 56.53%; H, 2.85%.

Step 2:
5-(2-Bromophenyl)-1,3-benzodioxole-4-carbaldehyde oxime (compound 15)

The process described in Method A was followed. 5-(2-Bromophenyl)-1,3-benzodioxole-4-carbaldehyde (0.350 g, 1.15 mmol) was used to obtain the title compound.

Work-up/purification: the reaction mixture was evaporated in vacuo to dryness, to the residue water was added and the aqueous phase was extracted with ethyl acetate. The combined organic phases were dried over anhydrous MgSO$_4$. The solvent was evaporated in vacuo. The crude product was purified by crystallization (two times) from a mixture of ethanol and water (4:1).

Yield: 0.139 g (38%), yellow crystals. Mp.: 168-169° C.

$^1$H NMR (DMSO-d$_6$): 6.15 (AB, 2H, CH$_2$, J=7.4, 1.0); 6.66 (d, 1H, Ar, J=8.0); 6.99 (d, 1H, Ar, J=8.0); 7.28-7.33 (m, 1H, Ar); 7.33-7.37 (m, 1H, Ar); 7.43-7.48 (m, 1H, Ar); 7.49 (s, 1H, OH—N=C—H); 7.70-7.74 (m, 1H, Ar); 11.37 (s, 1H, OH).

Analysis calculated for C$_{14}$H$_{16}$BrNO$_3$ (320.14): C, 52.52%; H, 3.15%; N, 4.38%. Found: C, 52.66%; H, 2.97%; N, 4.35%.

IV. Type 4 of Production Examples

Synthesis of 1,3-dimethyl-2,4-dioxo-1,2,3,4-tetrahydropyrimidine oximes (Procedure D)

IV.1: Example 16

6-Ethoxy-1,3-dimethyl-2,4-dioxo-1,2,3,4-tetrahydropyrimidine-5-carbaldehyde oxime (compound 16)

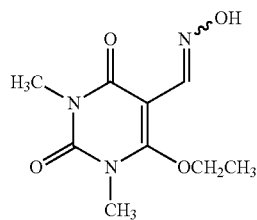

Step 1: 6-Ethoxy-1,3-dimethyl-2,4-dioxo-1,2,3,4-tetrahydropyrimidine-5-carbaldehyde (Method C, as a preferred embodiment of Procedure D, Scheme 5)

To a stirred solution of sodium (3.82 mmol) in ethanol (3.8 ml) under argon at 5-7° C., 6-chloro-1,3-dimethyl-2,4-dioxo-1,2,3,4-tetrahydropyrimidine-5-carbaldehyde (2.67 mmol) (Tetrahedron Lett., 1993, 34(51), 8213-8216) was added. The resulting mixture was stirred at room temperature under argon for 1 h. Then it was evaporated to dryness in vacuo and the residue was stirred in a mixture of ice-water (40 ml) and ethyl acetate (20 ml). After separation of the phases, the aqueous phase was extracted with ethyl acetate (20 ml). The combined organic phases were washed with water, brine and dried over anhydrous MgSO$_4$. The solvent was evaporated in vacuo, and the crude product was purified by column chromatography with a mixture of n-hexane:ethyl acetate (1:1) as the eluent.

Yield: 0.203 g (36%), white crystals. Mp.: 110-111° C.

$^1$H NMR (CDCl$_3$): 1.50 (t, 3H, CH$_3$); 3.38 (s, 3H, N—CH$_3$); 3.44 (s, 3H, N—CH$_3$); 4.54 (s, 2H, O—CH$_2$); 10.08 (s, 1H, CHO).

Analysis calculated for C$_9$H$_{12}$N$_2$O$_4$ (212.20): C, 50.94%; H, 5.70%; N, 13.20%. Found: C, 49.89%; H, 5.30%; N, 13.14%.

Step 2: 6-Ethoxy-1,3-dimethyl-2,4-dioxo-1,2,3,4-tetrahydropyrimidine-5-carbaldehyde oxime (compound 16)

The process described in Method A was followed. 6-Ethoxy-1,3-dimethyl-2,4-dioxo-1,2,3,4-tetrahydropyrimidine-5-carbaldehyde (0.386 g, 1.82 mmol) was used to obtain the title compound.

Work-up/purification: after evaporation of ethanol in vacuo, water was added to the residue. Then the precipitated crystals were filtered off and washed with water and n-pentane.

Yield: 0.256 g (62%), white crystals. Mp.: 115° C.

$^1$H NMR (DMSO-d$_6$): 1.34 (t, 3H, CH$_3$); 3.17 (s, 3H, N—CH$_3$); 3.29 (s, 3H, N—CH$_3$); 4.20 (q, 2H, CH$_2$); 7.89 (s, 1H, CH); 11.02 (s, 1H, N—OH).

Analysis calculated for C$_9$H$_{13}$N$_3$O$_4$ (227.22): C, 47.57%; H, 5.77%; N, 18.49%. Found: C, 47.49%; H, 5.66%; N, 18.34%.

IV.2: Example 17

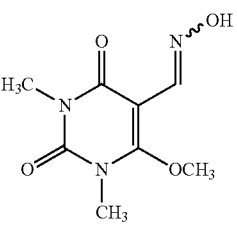

Step 1: 6-Methoxy-1,3-dimethyl-2,4-dioxo-1,2,3,4-tetrahydropyrimidine-5-carbaldehyde The process described in Method C was followed. 6-Chloro-1,3-dimethyl-2,4-dioxo-1,2,3,4-tetrahydropyrimidine-5-carbaldehyde (0.270 g, 1.33 mmol) and methanol were used to obtain the title compound. The crude product was purified by column chromatography with a mixture of n-hexane:ethyl acetate (4:1) as the eluent.

Yield: 0.089 g (34%), white crystals. Mp.: 105-107° C.

$^1$H NMR (CDCl$_3$): 3.38 (s, 3H, N—CH$_3$); 3.44 (s, 3H, N—CH$_3$); 4.25 (s, 3H, O—CH$_3$); 10.08 (s, 1H, CHO).

Analysis calculated for C$_8$H$_{10}$N$_2$O$_4$ (198.18): C, 48.48%; H, 5.09%; N, 14.14%. Found: C, 48.43%; H, 5.40%; N, 13.93%.

Step 2: 6-Methoxy-1,3-dimethyl-2,4-dioxo-1,2,3,4-tetrahydropyrimidine-5-carbaldehyde oxime (compound 17)

The process described in Method A was followed. 6-Methoxy-1,3-dimethyl-2,4-dioxo-1,2,3,4-tetrahydropyrimidine-5-carbaldehyde (0.125 g, 0.63 mmol) was used to obtain the title compound.

Work-up/purification: after evaporation of ethanol in vacuo, water was added to the residue. Then the precipitated crystals were filtered off. The crude product was purified by column chromatography with a mixture of chloroform:methanol (95:5) as the eluent.

Yield: 0.090 g (67%), white crystals. Mp.: 127-128° C.

$^1$H NMR (DMSO-d$_6$): 3.17 (s, 3H, N—CH$_3$); 3.29 (s, 3H, N—CH$_3$); 3.93 (s, 3H, O—CH$_3$); 7.90 (s, 1H, CH); 11.09 (s, 1H, N—OH).

Analysis calculated for $C_8H_{11}N_3O_4$ (213.19): C, 45.07%; H, 5.20%; N, 19.71%. Found: C, 44.46%; H, 5.07%; N, 19.20%.

IV.3: Example 18

1,3-Dimethyl-2,4-dioxo-6-propoxy-1,2,3,4-tetrahydropyrimidine-5-carbaldehyde oxime (compound 18)

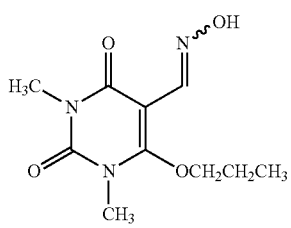

Step 1: 1,3-Dimethyl-2,4-dioxo-6-propoxy-1,2,3,4-tetrahydropyrimidine-5-carbaldehyde The process described in Method C was followed. 6-Chloro-1,3-dimethyl-2,4-dioxo-1,2,3,4-tetrahydropyrimidine-5-carbaldehyde (0.270 g, 1.33 mmol) and propanol were used to obtain the title compound. The crude product was purified by column chromatography with a mixture of n-hexane:ethyl acetate (1:1) as the eluent.

Yield: 0.118 g (40%), white crystals. Mp.: 57-58° C.

$^1$H NMR (CDCl$_3$): 1.04 (t, 3H, CH$_3$); 1.88 (sx, 2H, CH$_2$); 3.38 (s, 3H, N—CH$_3$); 3.45 (s, 3H, N—CH$_3$); 4.43 (t, 2H, O—CH$_2$); 10.06 (s, 1H, CHO).

Analysis calculated for $C_{10}H_{14}N_2O_4$ (226.23): C, 53.09%; H, 6.24%; N, 12.38%. Found: C, 53.04%; H, 7.02%; N, 12.42%.

Step 2: 1,3-Dimethyl-2,4-dioxo-6-propoxy-1,2,3,4-tetrahydropyrimidine-5-carbaldehyde oxime (compound 18)

The process described in Method A was followed. 1,3-Dimethyl-2,4-dioxo-6-propoxy-1,2,3,4-tetrahydropyrimidine-5-carbaldehyde (0.110 g, 0.48 mmol) was used to obtain the title compound.

Work-up/purification: after evaporation of ethanol in vacuo, water was added to the residue. Then the precipitated crystals were filtered off. The crude product was purified by column chromatography with a mixture of chloroform:methanol (9:1) as the eluent.

Yield: 0.086 g (73%), white crystals. Mp.: 119-120° C.

$^1$H NMR (DMSO-d$_6$): 0.95 (t, 3H, CH$_3$); 1.76 (sx, 2H, CH$_2$); 3.17 (s, 3H, N—CH$_3$); 3.30 (s, 3H, N—CH$_3$); 4.10 (t, 2H, O—CH$_2$); 7.88 (s, 1H, CH); 11.05 (s, 1H, N—OH).

Analysis calculated for $C_{10}H_{15}N_3O_4$ (241.24): C, 49.79%; H, 6.27%; N, 17.42%. Found: C, 49.33%; H, 6.10%; N, 17.08%.

IV.4: Example 19

6-Ethoxy-1,3-dimethyl-2,4-dioxo-1,2,3,4-tetrahydropyrimidine-5-carbaldehyde O-methyloxime (compound 19)

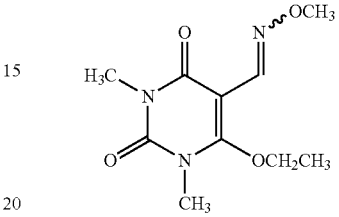

The process described in Method A was followed. 6-Ethoxy-1,3-dimethyl-2,4-dioxo-1,2,3,4-tetrahydropyrimidine-5-carbaldehyde (Example 16, Step 1) (0.168 g, 0.79 mmol) and methoxyamine hydrochloride (0.087 g, 1.04 mmol) were used to obtain the title compound.

Work-up/purification: after evaporation of ethanol in vacuo, water was added to the residue. Then the precipitated crystals were filtered off. The crude product was purified by column chromatography with a mixture of n-hexane:ethyl acetate (1:1) as the eluent.

Yield: 0.154 g (81%), white crystals. Mp.: 108-109° C.

$^1$H NMR (DMSO-d$_6$): 1.38 (t, 3H, CH$_3$); 3.17 (s, 3H, N—CH$_3$); 3.31 (s, 3H, N—CH$_3$); 3.83 (s, 3H, O—CH$_3$); 4.22 (q, 2H, O—CH$_2$); 7.97 (s, 1H, CH).

Analysis calculated for $C_{10}H_{15}N_3O_4$ (241.24): C, 49.79%; H, 6.27%; N, 17.42%. Found: C, 49.99%; H, 6.34%; N, 17.47%.

IV.5: Example 20

6-Ethoxy-1,3-dimethyl-2,4-dioxo-1,2,3,4-tetrahydropyrimidine-5-carbaldehyde O-benzyloxime (compound 20)

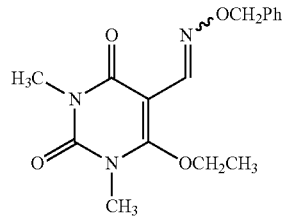

The process described in Method A was followed. 6-Ethoxy-1,3-dimethyl-2,4-dioxo-1,2,3,4-tetrahydropyrimidine-5-carbaldehyde (0.074 mg, 0.35 mmol) (Example 16, Step 1) and O-benzyl-hydroxyl-amine hydrochloride (0.073 mg, 0.46 mmol) were used to obtain the title compound.

Work-up/purification: after evaporation of ethanol in vacuo, water was added to the residue. Then the precipitated crystals were filtered off and washed with water and n-pentane.

Yield: 0.102 g (93%), white crystals. Mp.: 93-94° C.

¹H NMR (DMSO-d₆): 1.21 (t, 3H, CH₃); 3.16 (s, 3H, N—CH₃); 3.27 (s, 3H, N—CH₃); 4.05 (q, 2H, O—CH₂); 5.10 (s, 2H, N—CH—Ar); 7.27-7.39 (m, 5H, Ar); 8.06 (s, 1H, CH).

Analysis calculated for $C_{16}H_{19}N_3O_4$ (317.34): C, 60.56%; H, 6.03%; N, 13.24%. Found: C, 60.07%; H, 5.86%; N, 13.10%.

IV.6: Example 21

1,3-Dimethyl-2,4-dioxo-6-(propylthio)-1,2,3,4-tetrahydropyrimidine-5-carbaldehyde oxime (compound 21)

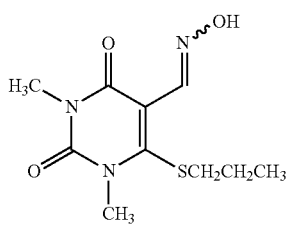

Step 1: 1,3-Dimethyl-2,4-dioxo-6-(propylthio)-1,2,3,4-tetrahydropyrimidine-5-carbaldehyde (Method D, as a preferred embodiment of Procedure D, Scheme 6)

To a stirred solution of propane-1-thiol (2.30 mmol) in dry 1,4-dioxane (4 ml), NaH (2.30 mmol) was added under argon. To the mixture, a solution of 6-chloro-1,3-dimethyl-2,4-dioxo-1,2,3,4-tetrahydropyrimidine-5-carbaldehyde (2 mmol) in dry 1,4-dioxane (8 ml) was added at 5-8° C. in one portion. The mixture was stirred at room temperature until the starting material was consumed (monitored by TLC). Then the mixture was poured onto ice water (50 ml) and the aqueous phase was extracted with ethyl acetate (3×30 ml). The combined organic phases were washed with water and dried over anhydrous MgSO₄. The solvent was evaporated in vacuo and the crude product was purified by column chromatography with a mixture of n-hexane:ethyl acetate (1:1) as the eluent.

Yield: 0.160 g (39%), pale yellow crystals. Mp.: 53-55° C.

¹H NMR (CDCl₃): 1.02 (t, 3H, CH₃); 1.69 (sx, 2H, CH₂); 3.02 (t, 2H, S—CH₂); 3.40 (s, 3H, N—CH₃); 3.72 (s, 3H, N—CH₃); 10.19 (s, 1H, CHO).

Analysis calculated for $C_{10}H_{14}N_2O_3S$ (242.29): C, 49.57%; H, 5.82%; N, 11.56%. Found: C, 49.22%; H, 6.33%; N, 11.72%.

Step 2: 1,3-Dimethyl-2,4-dioxo-6-(propylthio)-1,2,3,4-tetrahydropyrimidine-5-carbaldehyde oxime (compound 21)

The process described in Method A was followed. 1,3-Dimethyl-2,4-dioxo-6-(propylthio)-1,2,3,4-tetrahydropyrimidine-5-carbaldehyde (0.144 g, 0.60 mmol) was used to obtain the title compound.

Work-up/purification: after evaporation of ethanol in vacuo, water was added to the residue. Then the precipitated crystals were filtered off and washed with water and n-pentane.

Yield: 0.106 g (69%), white crystals. Mp.: 161-162° C.

¹H NMR (DMSO-d₆): 0.92 (t, 3H, CH₃); 1.54 (sx, 2H, CH₂); 2.89 (t, 2H, S—CH₂); 3.19 (s, 3H, N—CH₃); 3.58 (s, 3H, N—CH₃); 8.00 (s, 1H, CH); 11.29 (s, 1H, N—OH).

Analysis calculated for $C_{10}H_{15}N_3O_3S$ (257.31): C, 46.68%; H, 5.88%; N, 16.33%. Found: C, 46.49%; H, 5.54%; N, 16.32%.

IV.7: Example 22

1,3-Dimethyl-6-(methylthio)-2,4-dioxo-1,2,3,4-tetrahydropyrimidine-5-carbaldehyde oxime (compound 22)

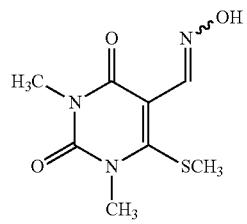

Step 1: 1,3-Dimethyl-6-(methylthio)-2,4-dioxo-1,2,3,4-tetrahydropyrimidine-5-carbaldehyde The process described in Method D was followed. 6-Chloro-1,3-dimethyl-2,4-dioxo-1,2,3,4-tetrahydropyrimidine-5-carbaldehyde (0.404 g, 2.00 mmol) and sodium thiomethoxide (0.154 g, 2.20 mmol in 4 ml 1,4-dioxane) were used to obtain the title compound. The crude product was purified by washing with n-pentane.

Yield: 0.302 g (70%), pale yellow crystals. Mp.: 104° C.

¹H NMR (CDCl₃): 2.58 (s, 3H, S—CH₃); 3.38 (s, 3H, N—CH₃); 3.69 (s, 3H, N—CH₃); 10.16 (s, 1H, CHO).

Analysis calculated for $C_8H_{10}N_2O_3S$ (214.24): C, 44.85%; H, 4.70%; N, 13.08%. Found: C, 44.80%; H, 4.82%; N, 13.05%.

Step 2: 1,3-Dimethyl-6-(methylthio)-2,4-dioxo-1,2,3,4-tetrahydropyrimidine-5-carbaldehyde oxime (compound 22)

The process described in Method A was followed. 1,3-Dimethyl-6-(methylthio)-2,4-dioxo-1,2,3,4-tetrahydropyrimidine-5-carbaldehyde (0.546 g, 2.55 mmol) was used to obtain the title compound.

Work-up/purification: after evaporation of ethanol in vacuo, water was added to the residue. Then the precipitated crystals were filtered off. The crude product was purified by column chromatography with a mixture of chloroform:methanol (9:1) as the eluent.

Yield: 0.443 g (76%), white crystals. Mp.: 165° C.

¹H NMR (DMSO-d₆): 2.43 (s, 3H, S—CH₃); 3.19 (s, 3H, N—CH₃); 3.58 (s, 3H, N—CH₃); 7.98 (s, 1H, CH); 11.29 (s, 1H, N—OH).

Analysis calculated for C$_8$H$_{11}$N$_3$O$_3$S (229.26): C, 41.91%; H, 4.84%; N, 18.33%. Found: C, 41.55%; H, 4.83%; N, 18.00%.

IV.8: Example 23

6-(Ethylthio)-1,3-dimethyl-2,4-dioxo-1,2,3,4-tetrahydropyrimidine-5-carbaldehyde oxime (compound 23)

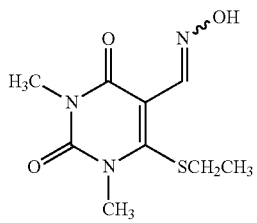

Step 1: 6-(Ethylthio)-1,3-dimethyl-2,4-dioxo-1,2,3,4-tetrahydropyrimidine-5-carbaldehyde The process described in Method D was followed. 6-Chloro-1,3-dimethyl-2,4-dioxo-1,2,3,4-tetrahydropyrimidine-5-carbaldehyde (0.303 g, 1.50 mmol) and ethanethiol were used to obtain the title compound. The crude product was purified by column chromatography with a mixture of n-hexane:ethyl acetate (1:1) as the eluent.

Yield: 0.102 g (30%), white crystals. Mp.: 72° C.

$^1$H NMR (CDCl$_3$): 1.32 (t, 3H, CH$_3$); 3.06 (q, 2H, CH$_2$); 3.38 (s, 3H, N—CH$_3$); 3.69 (s, 3H, N—CH$_3$); 10.18 (s, 1H, CHO).

Analysis calculated for C$_9$H$_{12}$N$_2$O$_3$S (228.27): C, 47.36%; H, 5.30%; N, 12.27%. Found: C, 47.24%; H, 5.35%; N, 12.20%.

Step 2: 6-(Ethylthio)-1,3-dimethyl-2,4-dioxo-1,2,3,4-tetrahydropyrimidine-5-carbaldehyde oxime (compound 23)

The process described in Method A was followed. 6-(Ethylthio)-1,3-dimethyl-2,4-dioxo-1,2,3,4-tetrahydropyrimidine-5-carbaldehyde (0.200 g, 0.87 mmol) was used to obtain the title compound.

Work-up/purification: after evaporation of ethanol in vacuo, water was added to the residue. Then the precipitated crystals were filtered off and washed with water and n-pentane.

Yield: 0.097 g (40%), white crystals. Mp.: 161-163° C.

$^1$H NMR (DMSO-d$_6$): 1.19 (t, 3H, CH$_3$); 2.93 (q, 2H, S—CH$_2$); 3.19 (s, 3H, N—CH$_3$); 3.58 (s, 3H, N—CH$_3$); 8.00 (s, 1H, CH); 11.29 (s, 1H, N—OH).

Analysis calculated for C$_9$H$_{13}$N$_3$O$_3$S (243.28): C, 44.43%; H, 5.39%; N, 17.27%. Found: C, 44.18%; H, 5.24%; N, 16.93%.

IV.9: Example 24

1,3-Dimethyl-2,4-dioxo-6-(phenylthio)-1,2,3,4-tetrahydropyrimidine-5-carbaldehyde oxime (compound 24)

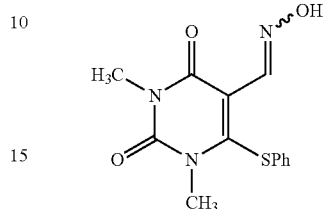

Step 1: 1,3-Dimethyl-2,4-dioxo-6-(phenylthio)-1,2,3,4-tetrahydropyrimidine-5-carbaldehyde The process described in Method D was followed. 6-Chloro-1,3-dimethyl-2,4-dioxo-1,2,3,4-tetrahydropyrimidine-5-carbaldehyde (1.50 g, 7.40 mmol) and benzenethiol were used to obtain the title compound.

Work-up/purification: the reaction mixture was evaporated to dryness and to the residue ethyl acetate (40 ml) was added. The organic phase was washed with water (3×40 ml) and dried over anhydrous MgSO$_4$. The crude product was purified by crystallization from a mixture of ethanol and diethyl ether (1:1).

Yield: 0.612 g (30%), beige crystals. Mp.: 132.4-133.5° C. (dec).

$^1$H NMR (DMSO-d$_6$): 3.21 (s, 3H, N—CH$_3$); 3.27 (s, 3H, N—CH$_3$); 7.30-7.55 (m, 5H, phenyl); 10.02 (s, 1H, CHO).

Analysis calculated for C$_{13}$H$_{12}$N$_2$O$_3$S (276.31): C, 56.51%; H, 4.38%; N, 10.14%. Found: C, 56.30%; H, 4.07%; N, 10.08%.

Step 2: 1,3-Dimethyl-2,4-dioxo-6-(phenylthio)-1,2,3,4-tetrahydropyrimidine-5-carbaldehyde oxime (compound 24)

The process described in Method A was followed. 1,3-Dimethyl-2,4-dioxo-6-(phenylthio)-1,2,3,4-tetrahydropyrimidine-5-carbaldehyde (0.400 g, 1.44 mmol) was used to obtain the title compound.

Work-up/purification: the precipitated crystals were filtered off and washed with water and ethanol. The crude product was purified by crystallization from a mixture of isopropyl alcohol and water (20:1).

Yield: 0.195 g (45%), pale yellow crystals. Mp.: 151.7-152.5° C.

$^1$H NMR (DMSO-d$_6$): 3.22 (s, 3H, N—CH$_3$); 3.24 (s, 3H, N—CH$_3$); 7.45-7.30 (m, 5H, phenyl); 7.99 (s, 1H, HO—N=C—H); 11.45 (1H, s, OH).

Analysis calculated for C$_{13}$H$_{13}$N$_3$O$_3$S (291.32): C, 53.60%; H, 4.50%; N, 14.42%. Found: C, 53.57%; H, 4.21%; N, 14.37%.

IV.10: Example 25

6-(Ethylthio)-1,3-dimethyl-2,4-dioxo-1,2,3,4-tetrahydropyrimidine-5-carbaldehyde O-methyloxime (compound 25)

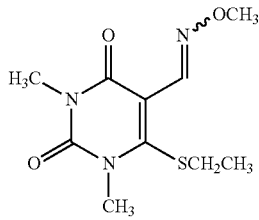

The process described in Method A was followed. 6-(Ethylthio)-1,3-dimethyl-2,4-dioxo-1,2,3,4-tetrahydropyrimidine-5-carbaldehyde (Example 23, Step 1) (0.148 mg, 0.65 mmol) and methoxyamine hydrochloride (0.072 mg, 0.86 mmol) were used to obtain the title compound.

Work-up/purification: after evaporation of ethanol in vacuo, water was added to the residue. Then the precipitated crystals were filtered off. The crude product was purified by column chromatography with a mixture of n-hexane:ethyl acetate (1:1) as the eluent.

Yield: 0.130 g (78%), white crystals. Mp.: 74-75° C. $^1$H NMR (DMSO-d$_6$): 1.20 (t, 3H, CH$_3$); 2.94 (q, 2H, CH$_2$); 3.19 (s, 3H, N—CH$_3$); 3.58 (s, 3H, N—CH$_3$); 3.84 (s, 3H, O—CH$_3$); 8.08 (s, 1H, CH).

Analysis calculated for C$_{10}$H$_{15}$N$_3$O$_3$S (257.31): C, 46.68%; H, 5.88%; N, 16.33%. Found: C, 46.81%; H, 5.80%; N, 16.32%.

IV.11: Example 26

6-(Ethylthio)-1,3-dimethyl-2,4-dioxo-1,2,3,4-tetrahydropyrimidine-5-carbaldehyde O-benzyloxime (compound 26)

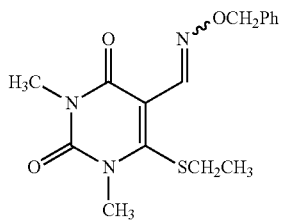

The process described in Method A was followed. 6-(Ethylthio)-1,3-dimethyl-2,4-dioxo-1,2,3,4-tetrahydropyrimidine-5-carbaldehyde (Example 23, Step 1) (0.070 mg, 0.30 mmol) and O-benzyl-hydroxylamine hydrochloride (0.063 mg, 0.40 mmol) were used to obtain the title compound.

Work-up/purification: after evaporation of ethanol in vacuo, water was added to the residue. Then the precipitated crystals were filtered off. The crude product was purified by column chromatography with a mixture of n-hexane:ethyl acetate (1:1) as the eluent.

Yield: 0.079 g (78%), white crystals. Mp.: 76° C. $^1$H NMR (DMSO-d$_6$): 1.13 (t, 3H, CH$_3$); 2.86 (q, 2H, S—CH$_2$); 3.18 (s, 3H, N—CH$_3$); 3.56 (s, 3H, N—CH$_3$); 5.12 (s, 2H, O—CH$_2$—Ar); 7.28-7.43 (m, 5H, Ar); 8.15 (s, 1H, CH).

Analysis calculated for C$_{16}$H$_{19}$N$_3$O$_3$S (333.41): C, 57.64%; H, 5.74%; N, 12.60%. Found: C, 57.62%; H, 5.48%; N, 12.61%.

IV.12: Example 27

6-[Allyl(methyl)amino]-1,3-dimethyl-2,4-dioxo-1,2,3,4-tetrahydropyrimidine-5-carbaldehyde oxime (compound 27)

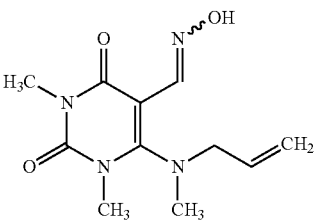 [SMILES: C=CCN(C)c1c(C=NO)c(=O)n(C)c(=O)n1C]

Step 1: 6-[Allyl(methyl)amino]-1,3-dimethyl-2,4-dioxo-1,2,3,4-tetrahydropyrimidine-5-carbaldehyde To a stirred solution of 6-chloro-1,3-dimethyl-2,4-dioxo-1,2,3,4-tetrahydropyrimidine-5-carbaldehyde (0.500 g, 2.47 mmol) and triethyl-amine (0.52 ml, 3.71 mmol) in dry ethanol (10 ml), N-methylprop-2-en-1-amine (0.36 ml, 3.71 mmol) was added under argon. The resulting mixture was stirred at room temperature under argon overnight. After evaporation of the solvent in vacuo, water (15 ml) was added to the yellow oily residue, and the mixture was extracted with dichloromethane (4×15 ml). The combined organic phases were dried over anhydrous MgSO$_4$. The solvent was evaporated in vacuo, and the crude product was purified by crystallization from a mixture of cyclohexane:isopropyl alcohol (4:1).

Yield: 0.330 g (55%), beige crystals. Mp.: 81.6-83.5° C.

$^1$H NMR (CDCl$_3$): 2.89 (s, 3H, N(6)CH$_3$); 3.35 (s, 3H, N—CH$_3$); 3.41 (s, 3H, N—CH$_3$); 3.78 (d, 2H, N—CH$_2$—CH=CH$_2$, J=3.4); 5.20-5.40 (m, 2H, N—CH$_2$—CH=CH$_2$); 5.65-5.75 (m, 1H, N—CH$_2$—CH=CH$_2$); 9.95 (s, 1H, CHO).

Analysis calculated for C$_{11}$H$_{15}$N$_3$O$_3$ (237.25): C, 55.69%; H, 6.37%; N, 17.71%. Found: C, 55.58%; H, 6.09%; N, 17.65%.

Step 2: 6-[Allyl(methyl)amino]-1,3-dimethyl-2,4-dioxo-1,2,3,4-tetrahydropyrimidine-5-carbaldehyde oxime (compound 27)

The process described in Method A was followed. 6-[Allyl (methyl)amino]-1,3-dimethyl-2,4-dioxo-1,2,3,4-tetrahydropyrimidine-5-carbaldehyde (0.120 g, 0.50 mmol) was used to obtain the title compound.

Work-up/purification: the precipitated crystals were filtered off. The crude product was purified by crystallization from a mixture of ethanol and water (2:1).

Yield: 0.022 g (55%), white crystals. Mp.: 95.5-97.1° C.

$^1$H NMR (DMSO-d$_6$): 2.61 (s, 3H, N(6)CH$_3$); 3.16 (s, 3H, N—CH$_3$); 3.32 (s, 3H, N—CH$_3$); 3.54 (d, 2H, N—CH$_2$—CH=CH$_2$, J=6.4); 5.05-5.15 (m, 2H, N—CH$_2$—CH=CH$_2$); 5.70-5.90 (m, 1H, N—CH$_2$—CH=CH$_2$); 7.88 (s, 1H, HO—N=C—H); 10.98 (s, 1H, OH).

Analysis calculated for $C_{11}H_{16}N_4O_3 \times 0.5\ H_2O$ (261.27): C, 50.57%; H, 6.56%; N, 21.44%. Found: C, 49.83%; H, 7.12%; N, 21.02%.

IV.13: Example 28

1,3-Dimethyl-2,4-dioxo-6-(4-phenylpiperazin-1-yl)-1,2,3,4-tetrahydropyrimidine-5-carbaldehyde oxime (compound 28)

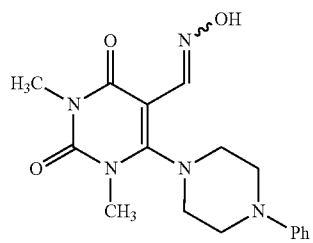 [SMILES: Cn1c(N2CCN(c3ccccc3)CC2)c(C=NO)c(=O)n(C)c1=O]

Step 1: 1,3-Dimethyl-2,4-dioxo-6-(4-phenylpiperazin-1-yl)-1,2,3,4-tetrahydropyrimidine-5-carbaldehyde To an ice-cooled, stirred solution of 6-chloro-1,3-dimethyl-2,4-dioxo-1,2,3,4-tetrahydropyrimidine-5-carbaldehyde (0.600 g, 2.96 mmol) and triethyl-amine (0.45 ml, 3.26 mmol) in dichloromethane (20 ml), a solution of N-phenylpiperazine (0.49 ml, 3.26 mmol) in dichloromethane (10 ml) was added dropwise. The resulting suspension was stirred at room temperature until the starting material was consumed (3.5 h, monitored by TLC). Then the reaction mixture was washed with water (3×10 ml), and the organic phase was dried over 20, anhydrous $MgSO_4$. The solvent was evaporated in vacuo, and the brown oily crude product was purified by column chromatography with a mixture of dichloromethane:ethyl acetate (1:1) as the eluent and crystallized from ethanol.

Yield: 0.710 g (73%), orange crystals. Mp.: 167.2-168.5° C.

$^1$H NMR ($CDCl_3$): 3.33-3.35 (m, 4H, N—$(CH_2)_2$); 3.36 (s, 3H, N—$CH_3$); 3.43-3.45 (m, 4H, N—$(CH_2)_2$); 3.51 (s, 3H, N—$CH_3$); 6.94-6.97 (m, 3H, Ar); 7.28-7.33 (m, 2H, Ar); 10.0 (s, 1H, CHO).

Analysis calculated for $C_{17}H_{20}N_4O_3$ (328.36): C, 62.18%; H, 6.14%; N, 17.06%. Found: C, 61.93%; H, 6.02%; N, 16.95%.

Step 2: 1,3-Dimethyl-2,4-dioxo-6-(4-phenylpiperazin-1-yl)-1,2,3,4-tetrahydropyrimidine-5-carbaldehyde oxime (compound 28)

The process described in Method A was followed. 1,3-Dimethyl-2,4-dioxo-6-(4-phenylpiperazin-1-yl)-1,2,3,4-tetrahydropyrimidine-5-carbaldehyde (0.400 g, 1.20 mmol) was used as starting material.

Work-up/purification: the precipitated crystals were filtered off and washed with water and ethanol. The crude product was purified by crystallization from a mixture of ethanol and water (4:1).

Yield: 0.153 g (37%), white crystals. Mp.: 173.4-174.3° C.

$^1$H NMR (DMSO-$d_6$): 3.07-3.14 (m, 4H, N($CH_2)_2$); 3.16 (s, 3H, N—$CH_3$); 3.30-3.37 (m, 4H, N($CH_2)_2$); 6.75-6.83 (m, 1H, H-4 phenyl); 6.90-7.10 (m, 2H, H-2, H-6 phenyl); 7.20-7.30 (m, 2H, H-3, H-5 phenyl); 7.92 (s, 1H, HO—N=C—H); 11.10 (1H, s, OH).

Analysis calculated for $C_{17}H_{21}N_5O_3$ (343.38): C, 59.46%; H, 6.16%; N, 20.40%. Found: C, 59.11%; H, 5.97%; N, 20.13%.

V. Type 5 of Production Examples

Synthesis of Pyridazinone Oximes (Procedure E)

V.1: Example 29

E-2-Methyl-3-oxo-5-piperidino-2,3-dihydropyridazine-4-carbaldehyde oxime (compound 29)

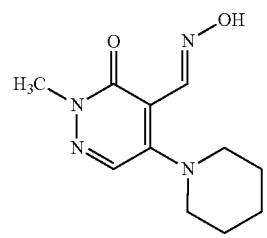 [SMILES: Cn1ncc(N2CCCCC2)c(/C=N/O)c1=O]

Step 1: 2-Methyl-3-oxo-5-piperidino-2,3-dihydropyridazine-4-carbaldehyde

A solution of 2-methyl-5-(piperidin-1-yl)pyridazin-3 (2H)-one [F. Farina, M. V. Martin and A. Tito, An. Quim., 77, 188-195 (1981)] (1.35 g, 7 mmol) in dry DMF (23.3 ml) was cooled to 5° C., then a solution of $POCl_3$ (1.44 ml, 15.4 mmol) in dry DMF (3.5 ml) was added dropwise. The cooling bath was removed and the mixture was stirred at room temperature for 30 min. Then, the temperature was raised to 70° C. and stirring was continued for 75 min. After cooling, the volatile components were removed under reduced pressure and the residue was treated with crushed ice (15 g). The mixture was adjusted to pH 7-8 with aqueous NaOH. Then it was extracted with dichloromethane (4×40 ml) and the combined extracts were washed with water, dried ($Na_2SO_4$) and evaporated. Residual volatile material was removed at $10^{-2}$ mbar to leave an oily residue which slowly solidified on storage in a refrigerator.

Yield: 1.35 g (87%), yellow-orange wax-like material. Mp.: 78-79° C.

$^1$H NMR (300 MHz, $CDCl_3$): 1.70-1.74 (m, 6H, $CH_2$); 3.39-3.42 (m, 4H, $NCH_2$); 3.64 (s, 3H, $NCH_3$); 7.69 (s, 1H, H-6); 10.16 (s, 1H, CHO).

Analysis calculated for $C_{11}H_{15}N_3O_2$ (221.26): C, 59.71%; H, 6.83%; N, 18.99%. Found: C, 59.80%; H, 6.83%; N, 18.81%.

Step 2: E-2-Methyl-3-oxo-5-piperidino-2,3-dihydropyridazine-4-carbaldehyde oxime (compound 29)

The process described in Method A was followed. 2-Methyl-3-oxo-5-piperidino-2,3-dihydropyridazine-4-carbaldehyde (663 mg, 3.00 mmol) was used to obtain the title compound. The reaction mixture was refluxed until the starting material was completely consumed (approx. 3 h; TLC monitoring: dichloromethane:methanol (9:1)).

Work-up/purification: the reaction mixture was evaporated to dryness under reduced pressure. After addition of water, the pH was adjusted to 7-8 with ammonia. The mixture was exhaustively extracted with dichloromethane and the combined extracts were washed with water, dried (Na$_2$SO$_4$) and evaporated. The crude product (containing an E/Z mixture) was recrystallized from ethyl acetate to afford the pure E isomer.

Yield: 326 mg (46%), pale yellow crystals. Mp.: 170-171° C.

$^1$H NMR (300 MHz, CDCl$_3$): 1.60-1.70 (m, 6H, CH$_2$); 3.18-3.23 (m, 4H, NCH$_2$); 3.73 (s, 3H, NCH$_3$); 7.65 (s, 1H, H-6); 8.06 (s, 1H, HO—N═C—H; shows NOE on irradiation at 11.31 ppm); 11.31 (br s, 1H, N—OH).

Analysis calculated for C$_{11}$H$_{16}$N$_4$O$_2$ (236.28): C, 55.92%; H, 6.83%; N, 23.71%. Found: C, 56.12%; H, 6.80%; N, 23.68%.

V.2: Example 30

E-2-Methyl-5-(4-methylpiperazin-1-yl)-3-oxo-2,3-dihydropyridazine-4-carbaldehyde oxime (compound 30)

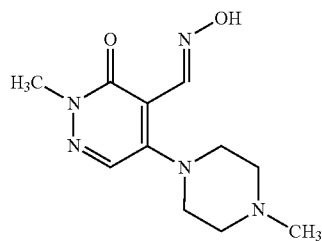

Step 1: 4-Chloro-2-methyl-5-(4-methylpiperazin-1-yl)pyridazin-3(2H)-one

A mixture of 4,5-dichloro-2-methylpyridazin-3(2H)-one [S.-F. Chen and R. P. Panzica, *J. Org. Chem.*, 46, 2467-2473 (1981)] (8.95 g, 50 mmol) and 1-methylpiperazine (12.5 g, 125 mmol) in water (150 ml) was refluxed for 30 h. After cooling, about two thirds of the solvent was removed under reduced pressure and the mixture was adjusted to pH 7-8 by addition of aqueous NaHCO$_3$. It was then extracted with dichloromethane (4×40 ml) and the combined extracts were washed with water, dried (Na$_2$SO$_4$) and evaporated. The crude product was purified by recrystallization from ethanol (95%).

Yield: 7.97 g (66%), colorless crystals. Mp.: 132-133° C.

$^1$H NMR (300 MHz, CDCl$_3$): 2.31 (s, 3H, piperazine NCH$_3$); 2.50-2.53 (m, 4H, CH$_2$); 3.36-3.39 (m, 4H, CH$_2$); 3.72 (s, 3H, pyridazine NCH$_3$); 7.55 (s, 1H, H-6).

Analysis calculated for C$_{10}$H$_{15}$ClN$_4$O (242.71): C, 49.49%; H, 6.23%; N, 23.08%. Found: C, 49.63%; H, 6.33%; N, 22.84%.

Step 2: 2-Methyl-5-(4-methylpiperazin-1-yl)pyridazin-3(2H)-one

To a mixture of 4-chloro-2-methyl-5-(4-methylpiperazin-1-yl)pyridazin-3(2H)-one (4.85 g, 20 mmol) and 10% Pd/C catalyst (1.14 g) in methanol (100 ml) was added ammonium formate (2.90 g, 46 mmol), and the mixture was refluxed under argon with TLC monitoring (dichloromethane:methanol (9:1)). Further portions of ammonium formate were added until the starting material was completely consumed. The catalyst was filtered off and washed with methanol, then the solvent was evaporated under reduced pressure. The residue was taken up in water (30 ml) and extracted with dichloromethane (4×40 ml). The combined extracts were washed with water, dried (Na$_2$SO$_4$) and evaporated. The crude product was purified by recrystallization from ethyl acetate:light petroleum.

Yield: 2.57 g (62%), colorless crystals. Mp.: 127-128° C.

$^1$H NMR (300 MHz, CDCl$_3$): 2.31 (s, 3H, piperazine NCH$_3$); 2.46-2.49 (m, 4H, CH$_2$); 3.26-3.30 (m, 4H, CH$_2$); 3.66 (s, 3H, pyridazine NCH$_3$); 5.88 (d, 1H, H-4, J=2.7); 7.60 (d, 1H, H-6, J=2.7).

Analysis calculated for C$_{10}$H$_{16}$N$_4$O (208.27): C, 57.67%; H, 7.74%; N, 26.90%. Found: C, 57.88%; H, 7.94%; N, 26.85%.

Step 3: 2-Methyl-5-(4-methylpiperazino)-3-oxo-2,3-dihydropyridazine-4-carbaldehyde A solution of 2-methyl-5-(4-methylpiperazin-1-yl)pyridazin-3(2H)-one (416 mg, 2 mmol) in dry DMF (6.7 ml) was cooled to 5° C., then a solution of POCl$_3$ (0.41 ml, 4.4 mmol) in dry DMF (1 ml) was added dropwise. The cooling bath was removed and the mixture was stirred at room temperature for 10 min. Then, the temperature was raised to 70° C. and stirring was continued for 75 min. After cooling, the volatile components were removed under reduced pressure and the residue was treated with crushed ice (15 g). The mixture was adjusted to pH 7-8 with aqueous NaOH. Then it was extracted with dichloromethane (4×40 ml) and the combined extracts were washed with water, dried (Na$_2$SO$_4$) and evaporated. Residual volatile material was removed at 10$^{-2}$ mbar to leave an oily residue which slowly solidified on storage in a refrigerator.

Yield: 376 mg (80%), yellowish wax-like material. Mp.: 85-102° C.

$^1$H NMR (300 MHz, CDCl$_3$): 2.32 (s, 3H, piperazine NCH$_3$); 2.55-2.59 (m, 4H, CH$_2$); 3.47-3.50 (m, 4H, CH$_2$); 3.67 (s, 3H, pyridazine NCH$_3$); 7.69 (s, 1H, H-6), 11.20 (s, 1H, CHO).

Analysis calculated for C$_{11}$H$_{16}$N$_4$O$_2$ (236.28): C, 55.92%; H, 6.83%; N, 23.71%. Found: C, 55.91%; H, 6.97%; N, 23.30%.

Step 4: E-2-Methyl-5-(4-methylpiperazin-1-yl)-3-oxo-2,3-dihydropyridazine-4-carbaldehyde oxime (compound 30)

The process described in Method A was followed. 2-Methyl-5-(4-methylpiperazino)-3-oxo-2,3-dihydropyridazine-4-carbaldehyde (472 mg, 2.00 mmol) was used to obtain the title compound. The reaction mixture was refluxed until the starting material was completely consumed (approx. 3 h; TLC monitoring: dichloromethane:methanol (9:1)).

Work-up/purification: the reaction mixture was evaporated in vacuo to dryness. After addition of water; the pH was adjusted to 7-8 with ammonia. The mixture was exhaustively extracted with dichloromethane and the combined extracts were washed with water, dried (Na$_2$SO$_4$) and evaporated. The crude product (containing an E/Z mixture) was recrystallized from ethyl acetate to afford the pure E isomer.

Yield: 240 mg (48%), colorless crystals. Mp.: 168-169° C.

$^1$H NMR (300 MHz, CDCl$_3$): 2.35 (s, 3H, piperazine NCH$_3$); 2.54-2.57 (m, 4H, CH$_2$); 3.33-3.36 (m, 4H, CH$_2$);

3.72 (s, 3H, pyridazine NCH₃); 7.65 (s, 1H, H-6); 8.25 (s, 1H, HO—N=C—H; shows NOE on irradiation at 11.65 ppm); 11.65 (br s, 1H, N—OH).

Analysis calculated for $C_{11}H_{17}N_5O_2$ (251.29): C, 52.58%; H, 6.82%; N, 27.87%. Found: C, 52.67%; H, 6.72%; N, 27.73%.

V.3: Example 31

E-2-Methyl-5-morpholino-3-oxo-6-phenyl-2,3-dihydropyridazine-4-carbaldehyde oxime (compound 31)

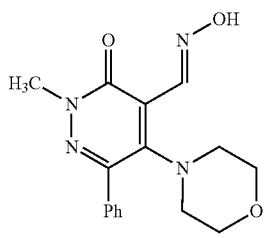

Step 1: 2-Methyl-5-morpholino-3-oxo-6-phenyl-2,3-dihydropyridazine-4-carbaldehyde The preparation of 2-methyl-5-morpholino-3-oxo-6-phenyl-2,3-dihydropyridazine-4-carbaldehyde starting from 5-chloro-2-methyl-6-phenylpyridazin-3(2H)-one is described by Dajka-Halász B. et al., *ARKIVOC* 2008 (iii), 102-126.

Step 2: 2-Methyl-5-morpholino-3-oxo-6-phenyl-2,3-dihydropyridazine-4-carbaldehyde oxime (compound 31)

The process described in Method A was followed. 2-Methyl-5-morpholino-3-oxo-6-phenyl-2,3-dihydropyridazine-4-carbaldehyde (0.500 g, 1.67 mmol) was used to obtain the title compound. The reaction mixture was heated under reflux for 17 h.

Work-up/purification: after evaporation of ethanol in vacuo, water was added to the residue. The mixture was extracted with dichloromethane. The combined organic phases were dried over anhydrous MgSO₄. The solvent was evaporated in vacuo. The crude product was purified by crystallization from 95% ethanol.

Yield: 0.208 g (35%), yellow crystals. Mp.: 182.4-183.2° C. ¹H NMR (DMSO-d₆): 2.72 (t, 4H, N—(CH₂)₂ morpholino, J=4.8); 3.36 (t, 4H, O—(CH₂)₂ morpholino, J=5.2); 3.61 (s, 3H, N(2)CH₃); 7.55-7.40 (m, 3H, Ar); 7.63-7.59 (m, 2H, Ar); 8.12 (s, 1H, HO—N=C—H); 11.59 (s, 1H, OH).

Analysis calculated for $C_{16}H_{18}N_4O_3$ (314.34): C, 61.13%; H, 5.77%; N, 17.82%. Found: C, 61.03%; H, 5.73%; N, 17.66%.

V.4: Example 32

E-2-(4-Methoxybenzyl)-5-morpholino-3-oxo-2,3-dihydropyridazine-4-carbaldehyde oxime (compound 32)

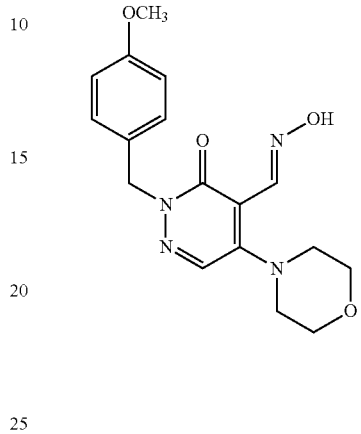

Step 1: 4-Chloro-2-(4-methoxybenzyl)-5-morpholinopyridazin-3(2H)-one

A mixture of 4,5-dichloro-2-(4-methoxybenzyl)pyridazin-3(2H)-one [P. Matyus, Gy. Rabloczky, L. Jaszlits, J. Kosary, M. Kurthy, A. Papp Behr, D. Zara, E. Karpati, A. Kovacs, WO1992/9212137] (10.15 g, 35.61 mmol) and morpholine (7.66 g, 87.92 mmol) in water (200 ml) was refluxed for 18 h. After cooling, the mixture was extracted with dichloromethane (4×40 ml) and the combined extracts were washed with water, dried (Na₂SO₄) and evaporated. The crude product was purified by recrystallization from ethanol (95%).

Yield: 8.66 g (72%), colorless crystals. Mp.: 125-127° C. ¹H NMR (300 MHz, DMSO-d₆): 3.35-3.38 (m, 4H, morpholine-CH₂); 3.66-3.69 (m, 4H, morpholine-CH₂); 3.71 (s, 3H, OCH₃); 5.13 (s, 2H, benzyl-CH₂); 6.86-6.88 (AA' part of an AA'BB' system, 2H, phenyl-H); 7.22-7.25 (BB' part of an AA'BB' system, 2H, phenyl-H); 7.91 (s, 1H, H-6).

Analysis calculated for $C_{16}H_{18}ClN_3O_3$ (335.79): C, 57.23%; H, 5.40%; N, 12.51%. Found: C, 57.03%; H, 5.42%; N, 12.59%.

Step 2: 2-(4-Methoxybenzyl)-5-morpholinopyridazin-3(2H)-one

To a mixture of 4-chloro-2-(4-methoxybenzyl)-5-(morpholin-4-yl)pyridazin-3(2H)-one (8.56 g, 25.50 mmol) and 10% Pd/C catalyst (1.45 g) in methanol (105 ml) was added ammonium formate (3.70 g, 58.7 mmol), and the mixture was refluxed under argon with TLC monitoring (ethyl acetate). Further portions of ammonium formate were added until the starting material was completely consumed. The catalyst was filtered off and washed with methanol, then the solvent was evaporated under reduced pressure. The residue was taken up in water (30 ml) and extracted with dichloromethane (4×40 ml). The combined extracts were washed with water, dried (Na₂SO₄) and evaporated. The crude product was purified by crystallization from ethanol (95%).

Yield: 4.25 g (85%), colorless crystals. Mp.: 132-133° C.

$^1$H NMR (300 MHz, DMSO-d$_6$): 3.26-3.29 (m, 4H, morpholine-CH$_2$); 3.64-3.67 (m, 4H, morpholine-CH$_2$); 3.71 (s, 3H, OCH$_3$); 5.05 (s, 2H, benzyl-CH$_2$); 5.85 (d, 1H, H-4, J=2.7 Hz); 6.84-6.87 (AA' part of an AA'BB' system, 2H, phenyl-H); 7.18-7.21 (BB' part of an AA'BB' system, 2H, phenyl-H); 7.96 (d, 1H, H-6, J=2.7 Hz).

Analysis calculated for C$_{16}$H$_{19}$N$_3$O$_3$ (301.35): C, 63.77%; H, 6.36%; N, 13.94%. Found: C, 63.79%; H, 6.38%; N, 14.11%.

Step 3: 2-(4-Methoxybenzyl)-5-morpholino-3-oxo-2,3-dihydropyridazine-4-carbaldehyde A solution of 2-(4-methoxybenzyl)-5-(morpholin-4-yl)pyridazin-3(2H)-one (6.22 g, 20.60 mmol) in dry DMF (60 ml) was cooled to 5° C., then a solution of POCl$_3$ (4.21 ml, 45.1 mmol) in dry DMF (12 ml) was added dropwise. The cooling bath was removed and the mixture was stirred at room temperature for 30 min. Then, the temperature was raised to 70° C. and stirring was continued for 80 min. After cooling, the volatile components were removed under reduced pressure and the residue was treated with crushed ice (70 g). The mixture was adjusted to pH 7-8 with aqueous NaOH. Then it was extracted with ethyl acetate (2×60 ml) and the combined extracts were washed with water, dried (Na$_2$SO$_4$) and evaporated. The crude product was purified by crystallization from ethanol (95%).

Yield: 6.09 g (90%), yellow crystals. Mp.: 130-132° C.

$^1$H NMR (300 MHz, DMSO-d$_6$): 3.44-3.47 (m, 4H, morpholine-CH$_2$); 3.70-3.73 (m, 7H, OCH$_3$, morpholine-CH$_2$); 5.07 (s, 2H, benzyl-CH$_2$Ph); 6.86-6.89 (AA' part of an AA'BB' system, 2H, phenyl-H); 7.23-7.27 (BB' part of an AA'BB' system, 2H, phenyl-H); 8.10 (s, 1H, H-6); 10.00 (s, 1H, CHO).

Analysis calculated for C$_{17}$H$_{19}$N$_3$O$_4$ (329.36): C, 62.00%; H, 5.81%; N, 12.76%. Found: C, 61.71%; H, 5.83%; N, 12.82%.

Step 4: E-2-(4-Methoxybenzyl)-5-morpholino-3-oxo-2,3-dihydropyridazine-4-carbaldehyde oxime (compound 32)

The process described in Method A was followed. 2-(4-Methoxybenzyl)-5-(morpholin-4-yl)-3-oxo-2,3-dihydro-pyridazine-4-carbaldehyde (1.69 g, 5.1 mmol) was used to obtain the title compound. The reaction mixture was refluxed until the starting material was completely consumed (approx. 3 h; TLC monitoring: ethyl acetate:methanol (19:1)).

Work-up/purification: the reaction mixture was evaporated in vacuo to dryness. After addition of water, the pH was adjusted to 7-8 with ammonia. The mixture was exhaustively extracted with dichloromethane and the combined extracts were washed with water, dried (Na$_2$SO$_4$) and evaporated. The crude product (containing an E/Z mixture) was recrystallized from ethanol (95%) to afford the pure E isomer.

Yield: 755 mg (43%), almost colorless crystals. Mp.: 166-168° C.

$^1$H NMR (300 MHz, DMSO-d$_6$): 3.20-3.24 (m, 4H, morpholine-CH$_2$); 3.63-3.67 (m, 4H, morpholine-CH$_2$); 3.71 (s, 3H, OCH$_3$); 5.08 (s, 2H, benzyl-CH$_2$); 6.85-6.88 (AA' part of an AA'BB' system, 2H, phenyl-H); 7.21-7.25 (BB' part of an AA'BB' system, 2H, phenyl-H); 7.94 (s, 1H, H-6); 8.17 (s, 1H, HO—N=C—H; shows NOE on irradiation at 11.34 ppm); 11.34 (br s, 1H, N—OH).

Analysis calculated for C$_{17}$H$_{20}$N$_4$O$_4$ (344.37): C, 59.25%; H, 5.85%; N, 16.27%. Found: C, 59.27%; H, 5.83%; N, 16.27%.

V.5: Example 33

2,5-Dimethyl-3-oxo-3,5,6,7-tetrahydro-2H-pyridazino[3,4-b][1,4]oxazine-4-carbaldehyde oxime (compound 33)

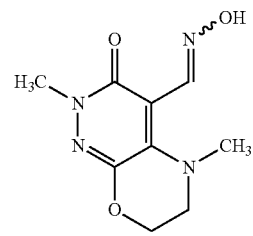

Step 1: 2,5-Dimethyl-3-oxo-3,5,6,7-tetrahydro-2H-pyridazino[3,4-b][1,4]oxazine-4-carbaldehyde 2,5-Dimethyl-3-oxo-3,5,6,7-tetrahydro-2H-pyridazino[3,4-b][1,4]oxazine-4-carbaldehyde can be synthesized by the method described by Elias O. et al *THEOCHEM*, 666-667, 625 (2003).

Step 2: 2,5-Dimethyl-3-oxo-3,5,6,7-tetrahydro-2H-pyridazino[3,4-b][1,4]oxazine-4-carbaldehyde oxime (compound 33)

The process described in Method A was followed. 2,5-Dimethyl-3-oxo-3,5,6,7-tetrahydro-2H-pyridazino[3,4-b][1,4]oxazine-4-carbaldehyde (0.800 g, 3.80 mmol) was used to obtain the title compound.

Work-up/purification: after evaporation of ethanol in vacuo, water was added to the residue. The mixture was extracted with dichloromethane. The combined organic phases were dried over anhydrous MgSO$_4$. The solvent was evaporated in vacuo. The crude product was purified by crystallization from 95% ethanol.

Yield: 0.270 g (31%), beige crystals. Mp.: 200.7-202.8° C. (dec).

$^1$H NMR (DMSO-d$_6$): 2.81 (s, 3H, N(5)CH$_3$); 3.38 (s, 3H, N(2)CH$_3$); 3.51 (t, 2H, H$_2$-6, J=4.8); 4.26 (t, 2H, H$_2$-7, J=4.8); 8.14 (s, 1H, HO—N=C—H); 11.12 (s, 1H, OH).

Analysis calculated for C$_9$H$_{12}$N$_4$O$_3$ (224.22): C, 48.21%; H, 5.39%; N, 24.99%. Found: C, 47.96%; H, 5.38%; N, 24.36%.

V.6: Example 34

5-Benzyl-2-methyl-3-oxo-3,5,6,7-tetrahydro-2H-pyridazino[3,4-b][1,4]oxazine-4-carbaldehyde oxime (compound 34)

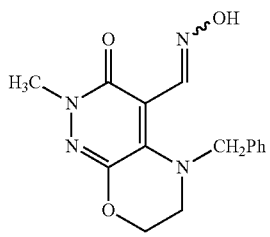

Step 1: 5-Benzyl-2-methyl-3-oxo-3,5,6,7-tetrahydro-2H-pyridazino[3,4-b][1,4]oxazine-4-carbaldehyde The preparation of 5-benzyl-2-methyl-3-oxo-3,5,6,7-tetrahydro-2H-pyridazino[3,4-b][1,4]oxazine-4-carbaldehyde is described by Elias O. et al *THEOCHEM*, 666-667, 625 (2003).

Step 2: 5-Benzyl-2-methyl-3-oxo-3,5,6,7-tetrahydro-2H-pyridazino[3,4-b][1,4]oxazine-4-carbaldehyde oxime (compound 34)

The process described in Method A was followed. 5-Benzyl-2-methyl-3-oxo-3,5,6,7-tetrahydro-2H-pyridazino[3,4-b][1,4]oxazine-4-carbaldehyde (1.00 g, 3.50 mmol) was used to obtain the title compound.

Work-up/purification: after evaporation of ethanol in vacuo, water was added to the residue. The mixture was extracted with dichloromethane. The combined organic phases were dried over anhydrous $MgSO_4$. The solvent was evaporated in vacuo. The crude product was purified by crystallization from 95% ethanol.

Yield: 0.550 g (53%), white crystals. Mp.: 225.0-228.2° C. (dec).

$^1$H NMR (DMSO-$d_6$): 3.35 (s, 3H, N(2)CH$_3$); 3.61 (t, 2H, H$_2$-6, J=5.2); 4.31 (t, 2H, H$_2$-7, J=5.2); 4.69 (s, 2H, CH$_2$—Ar); 7.00-7.15 (m, 2H, Ar); 7.20-7.40 (m, 3H, Ar); 7.74 (1H, s, HO—N=C—H); 11.29 (1H, s, OH).

Analysis calculated for $C_{15}H_{16}N_4O_3$ (300.31): C, 59.99%; H, 5.37%; N, 18.66%. Found: C, 59.66%; H, 5.21%; N, 18.53%.

V.7: Example 35

3-Methyl-2-oxo-2,3,6a,7,8,9-hexahydro-6H-pyridazino[3,4-b]pyrrolo[1,2-d][1,4]oxazine-1-carbaldehyde oxime (compound 35)

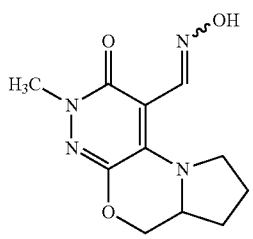

Step 1: 3-Methyl-2-oxo-2,3,6a,7,8,9-hexahydro-6H-pyridazino[3,4-b]pyrrolo[1,2-d][1,4]oxazine-1-carbaldehyde The preparation of 3-methyl-2-oxo-2,3,6a,7,8,9-hexahydro-6H-pyridazino[3,4-b]pyrrolo[1,2-d][1,4]oxazine-1-carbaldehyde is described by Elias O. et al *THEOCHEM*, 666-667, 625 (2003).

Step 2: 3-Methyl-2-oxo-2,3,6a,7,8,9-hexahydro-6H-pyridazino[3,4-b]pyrrolo[1,2-d][1,4]oxazine-1-carbaldehyde oxime (compound 35)

The process described in Method A was followed. 3-Methyl-2-oxo-2,3,6a,7,8,9-hexahydro-6H-pyridazino[3,4-b]pyrrolo[1,2-d][1,4]oxazine-1-carbaldehyde (0.235 g, 1.00 mmol) was used to obtain the title compound.

Work-up/purification: after evaporation of ethanol in vacuo, water was added to the residue. The mixture was extracted with dichloromethane. The combined organic phases were dried over anhydrous $MgSO_4$. The solvent was evaporated in vacuo. The crude product was purified by crystallization from 95% ethanol.

Yield: 0.193 g (77%), beige crystals. Mp.: 195-198° C. (dec).

$^1$H NMR (DMSO-$d_6$): δ 1.04-2.06 (m, 4H, CH$_2$); 3.02-3.44 (m, 1H, NCH$_2$); 3.40 (s, 3H, NCH$_3$); 3.64-3.85 (m, 2H, OCH$_{2a}$ and NCH); 4.47-4.57 (m, 1H, OCH$_{2b}$); 8.05 (s, 1H, CHN); 11.13 (s, 1H, NOH).

Analysis calculated for $C_{11}H_{14}N_4O_3$ (250.25): C, 52.79%; H, 5.64%; N, 22.39%. Found: C, 52.72%; H, 5.52%; N, 22.38%.

V.8: Example 36

5-Benzyl-2-methyl-3-oxo-2,3,5,6,7,8-hexahydropyridazino[3,4-b][1,4]oxazepine-4-carbaldehyde oxime (compound 36)

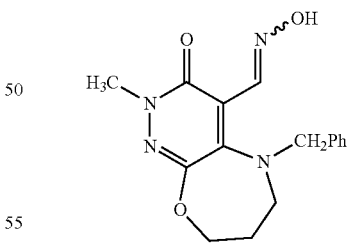

Step 1: 5-Benzyl-2-methyl-3-oxo-2,3,5,6,7,8-hexahydropyridazino[3,4-b][1,4]oxazepine-4-carbaldehyde The preparation of 5-benzyl-2-methyl-3-oxo-2,3,5,6,7,8-hexahydropyridazino[3,4-b][1,4]oxazepine-4-carbaldehyde is described by Elias O. et al *THEOCHEM*, 666-667, 625 (2003).

Step 2: 5-Benzyl-2-methyl-3-oxo-2,3,5,6,7,8-hexahydropyridazino[3,4-b][1,4]oxazepine-4-carbaldehyde oxime (compound 36)

The process described in Method A was followed. 5-Benzyl-2-methyl-3-oxo-2,3,5,6,7,8-hexahydropyridazino[3,4-b][1,4]oxazepine-4-carbaldehyde (1.00 g, 3.34 mmol) was used to obtain the title compound.

Work-up/purification: after evaporation of ethanol in vacuo, water was added to the residue. The mixture was extracted with dichloromethane. The combined organic phases were dried over anhydrous $MgSO_4$. The solvent was evaporated in vacuo. The crude product was purified by crystallization from 95% ethanol.

Yield: 0.690 g (67%), pale yellow crystals. Mp.: 178.7-180.6° C. (dec).

$^1$H NMR (DMSO-$d_6$): 1.91 (t, 2H, $H_2$-7, J=5.4); 3.26 (t, 2H, $H_2$-6, J=5.2); 3.43 (s, 3H, N(2)$CH_3$); 4.09 (t, 2H, $H_2$-8, J=6.0); 4.18 (s, 2H, $CH_2$—Ar); 7.35-7.15 (m, 5H, Ar); 8.03 (s, 1H, HO—N=C—H); 11.50 (s, 1H, OH).

Analysis calculated for $C_{16}H_{18}N_4O_3$ (314.34): C, 61.13%; H, 5.77%; N, 17.82%. Found: C, 61.13%; H, 6.62%; N, 17.72%.

V.9: Example 37

2-[5-(Dimethylamino)-2-methyl-3-oxo-2,3-dihydropyridazin-4-yl]benzaldehyde oxime (compound 37)

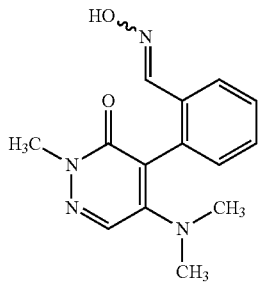 [SMILES: CN(C)c1cnn(C)c(=O)c1-c1ccccc1C=NO]

Step 1: 2-[5-(Dimethylamino)-2-methyl-3-oxo-2,3-dihydropyridazin-4-yl]benzaldehyde (Method E)

4-Chloro-5-(dimethylamino)-2-methylpyridazin-3(2H)-one (50.00 mmol) was dissolved in dimethoxyethane (155 ml), and Pd(PPh$_3$)$_4$ (1.60 g, 1.38 mmol) was added under argon. After stirring at room temperature for 10 min, 2-formylbenzeneboronic acid (10.50 g, 70.00 mmol) and 2M $Na_2CO_3$ solution (49.5 ml) were added. Subsequently, the reaction mixture was refluxed (oil bath temperature: 110° C.) for 15 h. The reaction was followed by TLC (eluent: chloroform:acetone (9:1)). Upon cooling the reaction mixture was poured onto ice (375 g), filtered over Celite and washed with chloroform (130 ml). The two layers were separated and the aqueous phase was extracted with chloroform (3×380 ml). The combined organic layers were washed with water (1×100 ml), dried over $MgSO_4$, filtered and purified by flash column chromatography with a mixture of diisopropyl ether and acetone (8:1) as the eluent and crystallized from a mixture of ethyl acetate and hexane (2.3:1).

Yield: 8.75 g (68%); yellow crystals. Mp.: 153-154° C.

$^1$H NMR (CDCl$_3$): 2.69 (s, 6H, N(CH$_3$)$_2$); 3.73 (s, 3H, NCH$_3$); 7.31 (dm, 1H, H-11, J=7.6); 7.46 (tm, 1H, H-13, J=7.6); 7.60 (tm, 1H, H-12, J=7.6); 7.74 (s, 1H, H-5); 7.96 (dm, 1H, H-14, J=7.6); 9.90 (d, 1H, CHO, J=0.7).

Analysis calculated for $C_{14}H_{15}N_3O_2$ (257.29): C, 65.35%; H, 5.88%; N, 16.33%. Found: C, 65.27%; H, 5.90%; N, 16.29%.

Step 2: 2-[5-(Dimethylamino)-2-methyl-3-oxo-2,3-dihydropyridazin-4-yl]benzaldehyde oxime (compound 37)

The process described in Method A was followed. 2-[5-(Dimethylamino)-2-methyl-3-oxo-2,3-dihydropyridazin-4-yl]benzaldehyde (1.00 g, 3.89 mmol) was used to obtain the title compound.

Work-up/purification: after evaporation of ethanol in vacuo, water was added to the residue. The mixture was extracted with dichloromethane. The combined organic phases were dried over anhydrous $MgSO_4$. The solvent was evaporated in vacuo. The crude product was purified by crystallization from 99% ethanol.

Yield: 1.01 g (96%), white crystals. Mp.: 202-203° C.

$^1$H NMR (DMSO-$d_6$): 2.60 (s, 6H, N(CH$_3$)$_2$); 3.57 (s, 3H, NCH$_3$); 7.11-7.15 (m, 1H, H-11); 7.30-7.40 (m, 2H, H-12, -13); 7.78 (dd, 1H, H-14, J=7.5, 1.9); 7.79 (s, 1H, H-16); 7.90 (s, 1H, H-5); 11.18 (s, 1H, H-18).

Analysis calculated for $C_{14}H_{16}N_4O_2$ (272.30): C, 61.75%; H, 5.92%; N, 20.58%. Found: C, 61.52%; H, 6.35%; N, 20.50%.

V.10: Example 38

2-(2-Methyl-3-oxo-5-pyrrolidino-2,3-dihydropyridazin-4-yl)benzaldehyde oxime (compound 38)

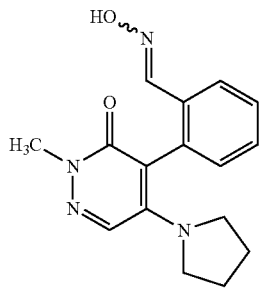 [SMILES: Cn1ncc(N2CCCC2)c(-c2ccccc2C=NO)c1=O]

Step 1: 2-(2-Methyl-3-oxo-5-pyrrolidino-2,3-dihydropyridazin-4-yl)benzaldehyde

The process described in Method E was followed. 4-Chloro-2-methyl-5-pyrrolidin-1-ylpyridazin-3(2H)-one was used to obtain the title compound.

Yield: 9.20 g (65%); yellow crystals. Mp.: 140-141° C.

$^1$H NMR (CDCl$_3$): 1.67-1.90 (m, 4H, pyrrolidine CH$_2$); 2.92-3.13 (m, 4H, pyrrolidine-NCH$_2$); 3.73 (s, 3H, NCH$_3$); 7.29 (dm, 1H, H-13, J=7.7); 7.45 (tm, 1H, H-15, J=7.7); 7.56 (td, 1H, H-14, J=7.7); 7.68 (s, 1H, H-7); 7.95 (dm, 1H, H-16, J=7.7); 9.96 (d, 1H, H-18, J=0.7).

Analysis calculated for $C_{16}H_{17}N_3O_2$ (283.33): C, 67.83%; H, 6.05%; N, 14.83%. Found: C, 67.73%; H, 6.12%; N, 14.86%.

Step 2: 2-(2-Methyl-3-oxo-5-pyrrolidino-2,3-dihydropyridazin-4-yl)benzaldehyde oxime (compound 38)

The process described in Method A was followed. 2-(2-Methyl-3-oxo-5-pyrrolidino-2,3-dihydropyridazin-4-yl)benzaldehyde (1.00 g, 3.53 mmol) was used to obtain the title compound.

Work-up/purification: the precipitated crystals were filtered off. The crude product was purified by crystallization from 99% ethanol.

Yield: 0.970 g (97%), white crystals. Mp.: 239° C.

$^1$H NMR (DMSO-$d_6$): 1.57-1.76 (m, 4H, pyrrolidine-CH$_2$); 2.88-3.02 (m, 4H, pyrrolidine-NCH$_2$); 3.56 (s, 3H, NCH$_3$); 7.10-7.16 (m, 1H, H-13); 7.29-7.38 (m, 2H, H-14, -15); 7.73-7.79 (m, 1H, H-16); 7.81 (s, 1H, H-18); 7.82 (s, 1H, H-7); 11.20 (s, 1H, H-20).

Analysis calculated for $C_{16}H_{18}N_4O_2 \cdot \frac{1}{6} H_2O$ (301.34): C, 63.77%; H, 6.13%; N, 18.59%. Found: C, 64.13%; H, 6.53%; N, 18.58%.

V.11: Example 39

2-(2-Methyl-3-oxo-5-piperidino-2,3-dihydropyridazin-4-yl)benzaldehyde oxime (compound 39)

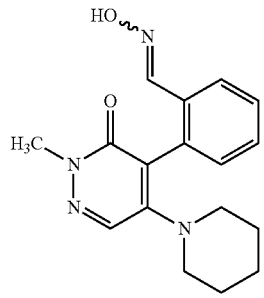 [SMILES: Cn1ncc(N2CCCCC2)c(-c2ccccc2C=NO)c1=O]

Step 1: 2-(2-Methyl-3-oxo-5-piperidino-2,3-dihydropyridazin-4-yl)benzaldehyde

The process described in Method E was followed. 4-Chloro-2-methyl-5-piperidin-1-ylpyridazin-3(2H)-one was used to obtain the title compound.

Yield: 9.07 g (61%), yellow crystals. Mp.: 134-135° C.

$^1$H NMR (CDCl$_3$): 1.29-1.58 (m, 6H, piperidine-CH$_2$); 2.84-3.04 (m, 4H, piperidine-NCH$_2$); 3.75 (s, 3H, NCH$_3$); 7.41 (dm, 1H, H-14, J=7.8); 7.46 (tm, 1H, H-16, J=7.8); 7.64 (tm, 1H, H-15, J=7.8); 7.72 (s, 1H, H-8); 7.98 (dm, 1H, H-17, J=7.8); 9.84 (s, 1H, H-19).

Analysis calculated for $C_{17}H_{19}N_3O_2$ (297.35): C, 68.67%; H, 6.44%; N, 14.13%. Found: C, 68.65%; H, 6.89%; N, 14.07%.

Step 2: 2-(2-Methyl-3-oxo-5-piperidino-2,3-dihydropyridazin-4-yl)benzaldehyde oxime (compound 39)

The process described in Method A was followed. 2-(2-Methyl-3-oxo-5-piperidino-2,3-dihydropyridazin-4-yl)benzaldehyde (1.00 g, 3.36 mmol) was used to obtain the title compound.

Work-up/purification: after evaporation of ethanol in vacuo, water was added to the residue. The mixture was extracted with dichloromethane. The combined organic phases were dried over anhydrous MgSO$_4$. The solvent was evaporated in vacuo. The crude product was purified by crystallization from 99% ethanol.

Yield: 1.02 g (97%), white crystals. Mp.: 184-185° C.

$^1$H NMR (DMSO-$d_6$): 1.23-1.33 (m, 4H, piperidine-CH$_2$); 1.34-1.43 (m, 2H, piperidine-CH$_2$); 2.81-2.98 (m, 4H, H-2, -6); 3.58 (s, 3H, NCH$_3$); 7.20 (dm, 1H, H-14, J=7.7); 7.35 (tm, 1H, H-16, J=7.7); 7.41 (td, 1H, H-15, J=7.7, 1.6); 7.75 (s, 1H, H-19); 7.82 (dm, 1H, H-17, J=7.7); 7.90 (s, 1H, H-8); 11.19 (s, 1H, H-21).

Analysis calculated for $C_{17}H_{20}N_4O_2$ (312.37): C, 65.37%; H, 6.45%; N, 17.94%. Found: C, 65.39%; H, 6.95%; N, 17.93%.

VI. Type 6 of Production Examples

Synthesis of Oxazole Oximes

VI.1: Example 40

3-(4,5-Diphenyl-1,3-oxazol-2-yl)propanal oxime (compound 40)

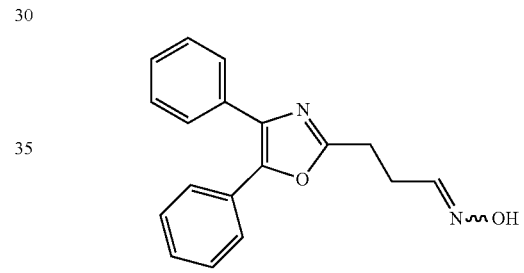

Step 1: 3-(4,5-Diphenyl-1,3-oxazol-2-yl)propanal

The synthesis of 3-(4,5-diphenyl-1,3-oxazol-2-yl)propanal is described by Pridgen L. N. et al in *Tetrahedron Lett.*, 25(27), 2835 (1984).

Step 2: 3-(4,5-Diphenyl-1,3-oxazol-2-yl)propanal oxime (compound 40)

The process described in Method A was followed. 3-(4,5-Diphenyl-1,3-oxazol-2-yl)propanal (277 mg, 1 mmol) was used to obtain the title compound.

Work-up/purification: after evaporation of ethanol in vacuo, water was added to the residue. Then the precipitated crystals were filtered off. The crude product was purified by column chromatography with a mixture of chloroform:ethyl acetate (95:5) as the eluent.

Yield: 195 mg (67%), yellow amorphous.

$^1$H NMR (CDCl$_3$): 2.73-2.82 (m, 2H, CH$_2$); 3.10-3.19 (m, 2H, CH$_2$); 7.28-7.42 (m, 6H, Ar & NCH); 7.52-7.68 (m, 5H, Ar); 8.56 (s, 1H, OH). Due to E/Z isomerism of the oxime, two signal sets appear in the $^1$H H NMR spectrum.

Analysis calculated for $C_{18}H_{16}N_2O_2$ (292.33): C, 73.96%; H, 5.52%; N, 9.58%. Found: C, 73.61%; H, 5.22%; N, 9.56%.

VI.2: Example 41

Ethyl({[3-(4,5-diphenyl-1,3-oxazol-2-yl)propylidene]amino}oxy)acetate (compound 41)

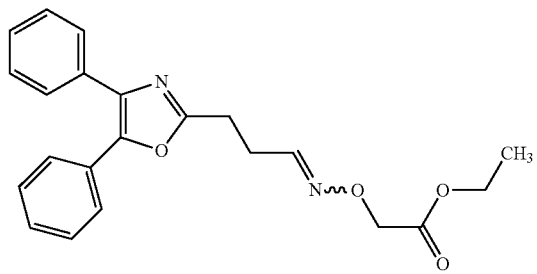 [SMILES: CCOC(=O)CON=CCCc1nc(-c2ccccc2)c(-c2ccccc2)o1]

To a stirred solution of 3-(4,5-diphenyl-1,3-oxazol-2-yl)propanal (500 mg, 1.71 mmol, see by Pridgen L. N. et al in *Tetrahedron Lett.*, 25(27), 2835 (1984)) in dry methyl ethyl ketone (10 ml), anhydrous $K_2CO_3$ (260 mg, 1.88 mmol) and ethyl bromoacetate (0.20 ml, 1.88 mmol) were added in one portion. The resulting suspension was stirred at reflux temperature (80° C.) until the starting material was consumed (2 h, monitored by TLC). The slurry was filtered off and the solvent was evaporated in vacuo. The brown oily crude product was purified by column chromatography with dichloromethane as eluent and crystallized from n-hexane.

Yield: 0.323 g (50%), white crystals. Mp.: 58-59.5° C.
$^1$H NMR (CDCl$_3$): 1.20 (t, 3H); 2.80 (m, 2H); 3.01 (m, 2H); 4.14 (q, 2H); 4.50/4.56 (s, 2H); 6.89/7.62 (t, 1H); 7.21-7.59 (m, 10H). Due to E/Z isomerism of the oxime two signal sets appear in the $^1$H NMR spectra.

Analysis calculated for $C_{22}H_{22}N_2O_4$ (378.42): C, 69.83%; H, 5.86%; N, 7.40%. Found: C, 69.67%; H, 5.81%; N, 7.32%.

VI.3: Example 42

3-(4,5-Diphenyl-1,3-oxazol-2-yl)propanal O-(phenylcarbamoyl)oxime (compound 42)

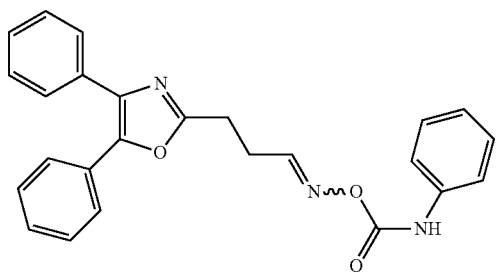 [SMILES: O=C(Nc1ccccc1)ON=CCCc1nc(-c2ccccc2)c(-c2ccccc2)o1]

To a cooled (ice and water bath) and stirred solution of 3-(4,5-diphenyl-1,3-oxazol-2-yl)propanal (300 mg, 1.02 mmol, Pridgen L. N. et al in *Tetrahedron Lett.*, 25(27), 2835 (1984)) in dry acetonitrile (10 ml), 2-3 drops of triethylamine was added. A solution of phenyl isocyanate in 2 ml of dry acetonitrile was added dropwise at such rate, that the internal temperature remained below 30° C. The resulting reaction mixture was stirred at room temperature until the starting material was consumed (19 h, monitored by TLC). The light precipitate was filtered off and the solvent was evaporated in vacuo. The yellow oily crude product was purified by column chromatography with dichloromethane as eluent and crystallized from n-hexane.

Yield: 0.193 g (45%), yellow crystals. Mp.: 117-118° C. (dec).
$^1$H NMR (CDCl$_3$): 2.98/3.10 (m, 2H); 3.14/3.22 (m, 2H); 7.32/7.96 (t, 1H); 7.02-7.68 (m, 15H); 8.05/8.14 (broad s, 1H). Due to E/Z isomerism of the oxime two signal sets appear in the $^1$H NMR spectra.

Analysis calculated for $C_{25}H_{21}N_3O_3$ (411.45): C, 72.98%; H, 5.14%; N, 10.21%. Found: C, 72.61%; H, 5.06%; N, 10.03%.

VI.4: Example 43

3-(4,5-Diphenyl-1,3-oxazol-2-yl)propanal O-(2-ethylpyrrolidine)oxime (compound 43)

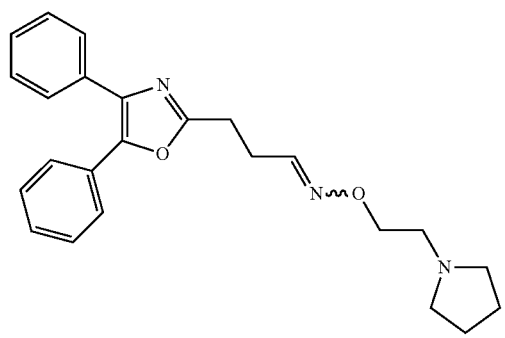 [SMILES: C(CCc1nc(-c2ccccc2)c(-c2ccccc2)o1)=NOCCN1CCCC1]

To a stirred solution of 3-(4,5-diphenyl-1,3-oxazol-2-yl)propanal (0.50 g, 1.71 mmol, see Pridgen L. N. et al in *Tetrahedron Lett.*, 25(27), 2835 (1984)) in dry methyl ethyl ketone (10 ml), anhydrous $K_2CO_3$ (2.12 g, 15.39 mmol) was added and the mixture was refluxed for 1 h. Then 1-(2-chloroethyl)pyrrolidine hydrochloride (0.87 g, 5.13 mmol) and a catalytic amount of NaOH were added and the reaction mixture was refluxed until the completion of the reaction (22 h, monitored by TLC, no more change observed). The slurry was filtered off and the solvent was evaporated in vacuo. The brown oily crude product was purified by column chromatography with chloroform:methanol (90:10) as eluent. (0.177 g unreacted starting material was isolated).

Yield: 0.288 g (43%), light yellow oil.
$^1$H NMR (CDCl$_3$): 1.78 (m, 4H); 2.59 (m, 4H); 2.77/2.81 (m, 2H); 2.77/2.88 (m, 2H); 3.05/3.08 (m, 2H); 4.19/4.27 (t, 2H); 6.86/7.57 (t, 1H); 7.28-7.68 (m, 10H). Due to E/Z isomerism of the oxime two signal sets appear in the $^1$H NMR spectra.

VI.5: Example 44

3-(4,5-Diphenyl-1,3-oxazol-2-yl)propanal O-(2-N,N-diethylethanamine)oxime (compound 44)

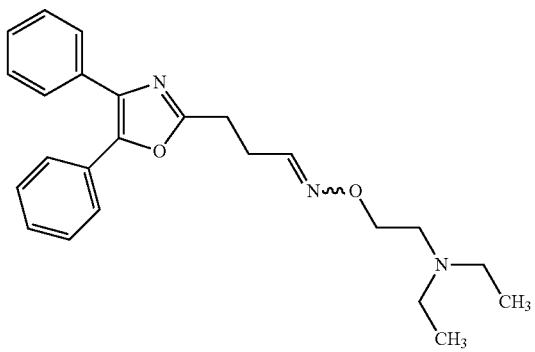 [SMILES: CCN(CC)CCON=CCCc1nc(-c2ccccc2)c(-c2ccccc2)o1]

To a stirred solution of 3-(4,5-diphenyl-1,3-oxazol-2-yl)propanal (0.50 g, 1.71 mmol, see Pridgen L. N. et al in *Tetrahedron Lett.*, 25(27), 2835 (1984)) in dry methyl ethyl ketone (10 ml), anhydrous $K_2CO_3$ (2.12 g, 15.39 mmol) was added and the mixture was refluxed for 1 h. Then 2-chloro-N,N-diethylethanamine hydrochloride (0.88 g, 5.13 mmol) and a catalytical amount of NaOH were added and the reaction mixture was refluxed until the completion of the reaction (22 h, monitored by TLC, no more change observed). The slurry was filtered off and the solvent was evaporated in vacuo. The brown oily crude product was purified by column chromatography with chloroform:methanol (90:10) as eluent. (0.156 g unreacted starting material was isolated).

Yield: 0.317 g (47%), light yellow oil.

$^1$H NMR (CDCl$_3$): 1.03/1.05 (m, 6H); 2.60/2.62 (m, 4H); 2.75/2.79 (m, 2H); 2.77/2.88 (m, 2H); 3.04/3.07 (m, 2H); 4.14/4.21 (t, 2H); 6.86/7.56 (t, 1H); 7.28-7.68 (m, 10H). Due to E/Z isomerism of the oxime two signal sets appear in the $^1$H NMR spectra.

VI.6: Example 45

3-(4,5-Diphenyl-1,3-oxazol-2-yl)-propionaldehyde O-benzyl-oxime (compound 45)

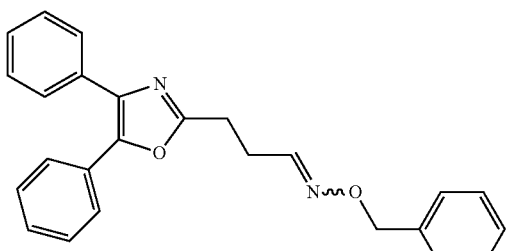

The process described in Method A was followed. 3-(4,5-Diphenyl-1,3-oxazol-2-yl)propanal (416 mg, 1.5 mmol, see Pridgen L. N. et al in *Tetrahedron Lett.*, 25(27), 2835 (1984)) and O-benzylhydroxylamine hydrochloride (319 mg, 2.0 mmol) were used to obtain the title compound.

Work-up/purification: after evaporation of ethanol in vacuo, water was added to the residue. The mixture was extracted with chloroform, dichloromethane and ethyl acetate. The combined organic phases were dried over anhydrous MgSO$_4$. The solvent was evaporated in vacuo. The crude product was purified by column chromatography with hexane:ethyl acetate (5:1) as eluent.

Yield: 488 mg (85%), yellow oil.

$^1$H NMR (CDCl$_3$): 2.74-2.81 (m, 1H); 2.89-2.95 (m, 1H); 3.03-3.10 (m, 2H); 5.06+5.13 (AB, 2H); 6.90 (t, 1H, J=5.2); 7.27-7.39 (m, 11H); 7.55-7.66 (m, 4H).

VI.7: Example 46

3-(4,5-Diphenyl-oxazol-2-yl)-propionaldehyde O-methyl-oxime (compound 46)

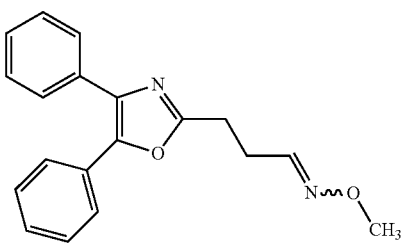 [SMILES: CON=CCCc1nc(-c2ccccc2)c(-c2ccccc2)o1]

The process described in Method A was followed. 3-(4,5-Diphenyl-1,3-oxazol-2-yl)propanal (554 mg, 2.0 mmol, see Pridgen L. N. et al in *Tetrahedron Lett.*, 25(27), 2835 (1984)) and methoxyamine hydrochloride (222 mg, 2.66 mmol) were used to obtain the title compound.

Work-up/purification: after evaporation of ethanol in vacuo, water was added to the residue. The mixture was extracted with chloroform, dichloromethane and ethyl acetate. The combined organic phases were dried over anhydrous MgSO$_4$. The solvent was evaporated in vacuo. The crude product was purified by column chromatography with hexane:ethyl acetate (5:1) as eluent.

Yield: 500 mg (82%), yellow oil.

$^1$H NMR (CDCl$_3$): 2.74-2.80 (m, 1H); 2.83-2.90 (m, 1H); 3.01-3.10 (m, 2H); 3.83+3.89 (s, 3H); 6.85 (t, 1H, J=5.2); 7.29-7.40 (m, 6H); 7.61-7.66 (m, 4H).

VII. Type 7 of Production Examples

Synthesis of Indole Oximes

VII.1: Example 47

1-(4-Chlorobenzoyl)-2-methyl-1H-indole-3-carbaldehyde oxime (compound 47)

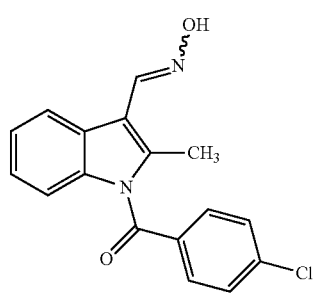 [SMILES: Cc1c(C=NO)c2ccccc2n1C(=O)c1ccc(Cl)cc1]

Step 1: 1-(4-Chlorobenzoyl)-2-methyl-1H-indole-3-carbaldehyde 1-(4-Chlorobenzoyl)-2-methyl-1H-indole-3-carbaldehyde can be prepared by an analogous method as 1-(4-chlorobenzoyl)-5-methoxy-2-methyl-1H-indole-3-carboxaldehyde, described in U.S. Pat. No. 4,981,865.

Step 2: 1-(4-Chlorobenzoyl)-2-methyl-1H-indole-3-carbaldehyde oxime

The process described in Method A was followed. The 1-(4-chlorobenzoyl)-2-methyl-1H-indole-3-carbaldehyde of Step 1 (200 mg, 0.67 mmol) was used to obtain the title compound.

Work-up/purification: the precipitated crystals were filtered off, washed with water, a mixture of n-pentane:ethyl acetate (95:5) and n-hexane.

Yield: 60 mg (28%), yellow crystals. Mp.: 152° C.

$^1$H NMR (CDCl$_3$): 2.51 (s, 3H, CH$_3$); 6.93 (d, 1H, Ar, J=8.3); 7.10-7.18 (m, 1H, Ar); 7.20-7.30 (m, 1H, Ar); 7.33 (br s, 1H, —CH=N—OH); 7.46-7.53 (m, 2H, Ar); 7.67-7.74 (m, 2H, Ar); 8.10 (d, 1H, Ar, J=7.8); 8.44 (s, 1H, OH).

HRMS calculated for C$_{17}$H$_{13}$ClN$_2$O$_2$+H$^+$: 313.0743. Found: 313.0735.

Test Example 1

In Vitro Inhibition of SSAO Activity on Human Recombinant VAP-1

For determining the SSAO/VAP-1 activity, the colorimetric method described by Holt, A (Holt, A., Anal. Biochem. 244, 384, 1997) for monoamine oxidase and analogous enzymes was used. Recombinant SSAO/VAP-1 enzyme was expressed in Chinese Hamster Ovary cells (CHO). These cells and cell cultures have been described earlier (Smith, D. J. et al, J. Exp. Med. 188, 17, 1998). The cell homogenate was prepared as follows: a suspension was made of approximately 3.6×10$^8$ cells in 25 ml lysation buffer (150 mM NaCl, 10 mM Tris-base pH 7.2, 1.5 mM MgCl$_2$, 1% NP40), that was stirred for 1 night and incubated at 4° C. The homogenate was centrifugated (18000 g). The supernatant was used directly afterwards for the measurement. SSAO/VAP-1 activity measurement was carried out as follows on 96 precisely microtitrated plates, a given amount of inhibitor was added to each. The amount of the inhibitors varied among the measurements, the final concentration being between 1 nM and 50 µM in general, in 20 µl aqueous total volume for all cases. Then 0.2 M potassium phosphate buffer (pH=7.6) was added, to obtain a total volume of 200 µl 50 µl freshly prepared chromogen solution was given, which contains 1 mM of vanillic acid, 500 µM 4-aminoantipyrin, 8 U/ml horse radish peroxidase, and such an amount of SSAO/VAP-1 containing CHO cell homogenate that causes a 0.6 A$_{490}$ per h change, the latter being in the linear coherence scope of the method. The plates were incubated for 30 min at 37° C. and the background absorbance was measured at 490 nm by a Wallac Victor II apparatus. For starting the enzyme reaction, 20 µl 10 mM benzyl amine solution was added, the final concentration of which was therefore 1 mM. The plates were reincubated at 37° C. for 1 h. The increase in the absorbance showing the SSAO/VAP-1 activity was measured at 490 nm. The inhibition was calculated in the % of the control absorbance corrected with the background absorbance, IC$_{50}$ values were calculated using GraphPad Prism.

SSAO/VAP-1 inhibitory effects (IC$_{50}$ values or in some cases, % inhibition at a given concentration) of representative compounds according to the present invention are listed in the following table. Numbers in the table respectively correspond to the compound numbers in Production Examples described above.

TABLE 1

| Compound No. | IC$_{50}$ (µM) or % inhibition |
|---|---|
| 1 | 102 |
| 5 | 32% (50 µM) |
| 6 | 4.3 |
| 7 | 40 |
| 8 | 95 |
| 9 | 14.9 |
| 10 | 35% (500 µM) |
| 12 | 180 |
| 16 | 53 |
| 17 | 30 |
| 18 | 18 |
| 19 | 29 |
| 21 | 58 |
| 22 | 48 |
| 23 | 111 |
| 24 | 106 |
| 25 | 113 |
| 27 | 41 |
| 29 | 240 |
| 32 | 263 |
| 35 | 55% (500 µM) |
| 38 | 31% (500 µM) |
| 40 | 3.5 |

Test Example 2

Inhibition of Carrageenan-Induced Rat Paw Edema

Carrageenan-induced rat paw edema has been extensively used in the evaluation of anti-inflammatory effects of various agents and it is useful in assessing the efficacy of compounds to alleviate acute inflammation (Whiteley P E, Dalrymple S A (1998) Models of inflammation: carrageenan-induced paw edema in the rat, in Current Protocols in Pharmacology (Enna S J, Williams M, Ferkany J W, Kenakin T, Porsolt R E, Sullivan J P eds) pp 5.4.1-5.4.3, John Wiley & Sons, New York.). Edema in the paws was induced by injecting 0.1 ml of a 1% solution of carrageenan intraplantary. The size of the edema was measured with a plethysmographic (Ugo-Basil) method 3 hours after injection of carrageenan solution. Compounds of the invention were administered subcutaneously (s.c.) and orally (p.o.) 60, or 30 minutes prior to carrageenan exposure. Inhibitory effects are expressed in % values.

TABLE 2

| Compound No. | Dose mg/kg | | n | Inhibition of rat paw edema in % | | |
|---|---|---|---|---|---|---|
| | | | | 60 min | 120 min | 180 min |
| 9 | 30 | s.c. | 10 | 54 ± 6* | 40 ± 5* | 50 ± 5* |
| | 15 | s.c. | 5 | 53 ± 5* | 52 ± 3* | 66 ± 7** |
| | 7.5 | s.c. | 5 | 63 ± 7* | 62 ± 6* | 66 ± 5** |
| | 30 | p.o. | 5 | 0 | 5 ± 1 | 0 |
| 16 | 30 | s.c. | 10 | 8 ± 1 | 19 ± 2 | 31 ± 4 |
| 22 | 30 | s.c. | 10 | 58 ± 7* | 54 ± 5* | 72 ± 8** |
| | 15 | s.c. | 5 | 60 ± 6* | 63 ± 7** | 65 ± 7** |
| | 7.5 | s.c. | 5 | 15 ± 2 | 55 ± 5* | 60 ± 5* |
| | 30 | p.o. | 5 | 0 | 21 ± 2 | 21 ± 2 |

TABLE 2-continued

| Compound No. | Dose mg/kg | Inhibition of rat paw edema in % | | | |
|---|---|---|---|---|---|
| | | n | 60 min | 120 min | 180 min |
| Indomethacin | 2.5 p.o. | 5 | 32 ± 2* | 51 ± 4* | 53 ± 5** |
| Solvent | | 10 | 0 | 0 | 10 ± 1 |

*p < 0.05
**p < 0.01 (ANOVA, Newmann-Keuls post hoc test)

Test Example 3

Inhibition of Acetic Acid Induced Writhing on Mice

The method described by Van der Wende (Van der Vende C, Margolin S, Fed. Proc., 15, 494, 1956) with the modifications of Witkin et al. (Witkin L B et al, J. Pharm. Exp. Ther., 133, 400, 1961) was applied. 0.2 ml of a 0.6% acetic acid solution was injected intraperitoneally, causing a typical writhing syndrome in 90% of the animals. Compounds of the invention were administered subcutaneously, 20 minutes prior to acetic acid exposure. Antianalgetic effect was determined by the formula, which is shown below, and is expressed in % values.

(number of writhings in treatment group (5')/number of writhings in control group (5'))×100

TABLE 3

| Compound No. | Dose mg/kg | Inhibition of writhing syndrome in % |
|---|---|---|
| 9 | 30 s.c. | 80 ± 7** |
| | 15 s.c. | 84 ± 8** |
| 16 | 30 s.c. | 96 ± 6** |
| | 15 s.c. | 86 ± 7** |
| 22 | 15 s.c. | 100 |
| | 5 s.c. | 70 ± 5** |
| Solvent | s.c. | 10 ± 1 |

*p < 0.01
**p < 0.05 (ANOVA, Newmann-Keuls post hoc test), n = 5

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A compound of general formula of Ar—$(CH_2)_n$—$CR^1$=N—$OR^2$ (I) or salt, hydrate or solvate thereof, wherein
Ar is a group of the formula:

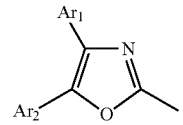

$R^1$ is H or lower alkyl;
$R^2$ is H, lower alkyl, benzyl, —$(CH_2)_k$—$COOR^{13}$, —$(CH_2)_m$—$N(R^{14}R^{15})$ or —CO—NH—$R^{16}$,
wherein $R^{13}$ is lower alkyl,
k is 1, 2 or 3;
m is 1, 2 or 3;
$R^{14}$ and $R^{15}$ are independently from each other lower alkyl, or $R^{14}$ and $R^{15}$ together with the nitrogen they are attached form a 5 to 7 membered heterering, optionally containing 1 to 3 further heteroatom(s) selected from nitrogen, oxygen and sulfur atoms,
$R^{16}$ is phenyl, optionally substituted with one or more group selected from halogen, lower alkyl and lower alkoxy;
n is integer of 0 to 4;
$Ar^1$ and $Ar^2$ are the same or different and stand for phenyl, optionally substituted with one or more group selected from halogen, lower alkyl and lower alkoxy.

2. A compound according to claim 1, wherein $R^{14}$ and $R^{15}$ are methyl, or $R^{14}$ and $R^{15}$ together with the nitrogen they are attached to form a pyrrolidine ring.

3. A compound of claim 1, which is 3-(4,5-diphenyl-1,3-oxazol-2-yl)propanal oxime or any hydrate, solvate or salt thereof.

4. A compound according to claim 1, which is 3-(4,5-diphenyl-1,3-oxazol-2-yl)propanal oxime.

5. A pharmaceutical composition, which comprises, as an active ingredient, one or more compound(s) of claim 1 or a pharmaceutically acceptable salt thereof in admixture with one or more pharmaceutically acceptable auxiliary/auxiliaries.

6. The compound of claim 1, or salt, hydrate or solvate thereof, wherein k is 1.

7. The compound of claim 1, or salt, hydrate or solvate thereof, wherein m is 2.

8. The compound of claim 1, or salt, hydrate or solvate thereof, wherein n is 0, 1 or 2.

9. The compound of claim 1, or salt, hydrate or solvate thereof, wherein $Ar^1$ and $Ar^2$ are both phenyl.

10. The compound of claim 1 of general formula of Ar—$(CH_2)_n$—$CR^1$=N—$OR^2$ (I), or a salt or hydrate thereof.

11. The compound of claim 1 of general formula of Ar—$(CH_2)_n$—$CR^1$=N—$OR^2$ (I), or a salt thereof.

12. The compound of claim 1 of general formula of Ar—$(CH_2)_n$—$CR^1$=N—$OR^2$ (1), or a solution thereof.

* * * * *